US012611642B2

(12) United States Patent
Lee et al.

(10) Patent No.: US 12,611,642 B2
(45) Date of Patent: Apr. 28, 2026

(54) ADAPTER AND METHOD OF MIXING CONSTITUENTS OF A PHARMACEUTICAL COMPLEX VIA AN ADAPTER

(71) Applicant: West Pharmaceutical Services, Inc., Exton, PA (US)

(72) Inventors: Claudia Lee, Merion Station, PA (US); Michael Sullivan, Birdsboro, PA (US); Rajiv Kumar, Chester Springs, PA (US); Daniel E. Delvecchio, Scottsdale, AZ (US); James Guthlein, Malvern, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 835 days.

(21) Appl. No.: 17/960,027

(22) Filed: Oct. 4, 2022

(65) Prior Publication Data

US 2023/0105059 A1     Apr. 6, 2023

Related U.S. Application Data

(60) Provisional application No. 63/251,880, filed on Oct. 4, 2021.

(51) Int. Cl.
    *B01F 33/00*        (2022.01)
    *A61K 47/69*        (2017.01)
        (Continued)

(52) U.S. Cl.
    CPC ........ *B01F 33/301* (2022.01); *A61K 47/6929* (2017.08); *B01F 23/405* (2022.01);
        (Continued)

(58) Field of Classification Search
    CPC ................ B01F 33/301; B01F 25/4331; B01F 35/75425; A61K 47/6929
    See application file for complete search history.

(56) References Cited

U.S. PATENT DOCUMENTS

| | | | |
|---|---|---|---|
| 8,753,325 B2 | 6/2014 | Lev et al. | |
| 2010/0042044 A1 | 2/2010 | Middleton et al. | |
| (Continued) | | | |

FOREIGN PATENT DOCUMENTS

| | | |
|---|---|---|
| CN | 206103829 U | 4/2017 |
| JP | 2004317439 A | 11/2004 |
| (Continued) | | |

OTHER PUBLICATIONS

International Search Report and Written Opinion dated Jan. 13, 2023 from corresponding Application No. PCT/US2022/045696.

*Primary Examiner* — Anshu Bhatia
(74) *Attorney, Agent, or Firm* — Blank Rome LLP

(57) ABSTRACT

An adapter for connecting one or more storage containers with a syringe is described. The adapter includes a first port that provide a connection with a first container volume, a second port that provides a connection with a second container volume, a third port that provides a connection to a syringe. The adapter further includes a mixing channel extending from a first end in fluid communication with the third port to a second end. The mixing channel includes a tortuous path along at least a portion of its length. The mixing channel enables two constituents of a pharmaceutical complex to be mixed through the mixing channel to form the pharmaceutical complex. Also disclosed is a system including such an adapter, a method of mixing two constituents of a pharmaceutical complex via such an adapter and a method of manufacturing such an adapter.

20 Claims, 11 Drawing Sheets

(51) Int. Cl.

| | | |
|---|---|---|
| *B01F 23/40* | (2022.01) |
| *B01F 23/45* | (2022.01) |
| *B01F 25/433* | (2022.01) |
| *B01F 33/301* | (2022.01) |
| *B01F 35/75* | (2022.01) |
| *B01F 101/22* | (2022.01) |

(52) U.S. Cl.

CPC .......... *B01F 23/45* (2022.01); *B01F 25/4331* (2022.01); *B01F 35/75425* (2022.01); *B01F 2101/22* (2022.01)

(56) References Cited

U.S. PATENT DOCUMENTS

| | | | |
|---|---|---|---|
| 2012/0029464 A1* | 2/2012 | Kragelund ............ | A61J 1/2089 |
| | | | 604/414 |
| 2013/0236375 A1 | 9/2013 | Tan et al. | |
| 2018/0111830 A1* | 4/2018 | Wild ................... | B01F 25/4317 |

FOREIGN PATENT DOCUMENTS

| | | | |
|---|---|---|---|
| JP | 2005199245 A | 7/2005 |
| JP | 2007136322 A | 6/2007 |
| JP | 2009233483 A | 10/2009 |
| JP | 2016041426 A | 3/2016 |
| WO | 2011077434 A1 | 6/2011 |

* cited by examiner

500b

502b — Depress the plunger of the syringe

504 — Connect syringe to the third port of the adapter

506b — Connect containers to the ports of an adapter

508 — Withdraw the plunger of the syringe

500a

502a — Connect containers to the ports of an adapter

504 — Connect syringe to the third port of the adapter

506a — Depress the plunger of the syringe

508 — Withdraw the plunger of the syringe

700

702 — Fashion a first depression in a first piece

704 — Fashion a second depression in a second piece

706 — Fuse the first piece to the second piece

FIG. 11A            FIG. 11B

ADAPTER AND METHOD OF MIXING CONSTITUENTS OF A PHARMACEUTICAL COMPLEX VIA AN ADAPTER

CROSS REFERENCE TO RELATED APPLICATIONS

This application claims the benefit of U.S. Provisional Patent App. No. 63/251,880, filed Oct. 4, 2021, the disclosure of which is hereby incorporated by reference herein.

TECHNICAL FIELD

The disclosure relates to adapters for connecting one or more storage containers with a syringe, systems comprising such adapters, methods of mixing constituents of a pharmaceutical complex via such adapters, and methods of manufacturing such adapters.

BACKGROUND

Recent developments in immunology include newly-approved messenger RNA-lipid nanoparticle (mRNA-LNP) vaccines. Messenger RNA (mRNA) technology has the advantage of being able to rapidly adapt to new antigen designs by altering the mRNA sequence without needing to overhaul the Chemical & Manufacturing Control (CMC) of the vaccine production. However, mRNA provided alone is not readily absorbed or delivered effectively to human immune cells, has unstable chemical and physical properties and therefore is not effective for use as a vaccine. Recent developments have shown that absorption and stability of mRNA can be increased to effective levels if it is encapsulated within lipid nanoparticle (LNP) vectors.

Preparation of mRNA-LNP vaccines is achieved by mixing ethanol dissolved lipids with RNA in water, under closely controlled conditions. Such mixing is usually carried out in a laboratory using devices which are often inappropriate for high-scale distribution (due, for instance, to their low durability, high cost, high complexity, low lot-to-lot consistency and/or high inter-batch variation).

The shelf life of mRNA-LNP at room temperature is limited. To extend their shelf life, mRNA-LNP vaccines must therefore be stored at extremely low temperatures (typically −20 to −80 degrees Celsius). This is a problem because low temperature distribution is expensive and logistically complex. Additionally, there is a risk of mRNA-LNP vaccines being wasted if, for example, the low-temperature environment at any stage in the distribution chain were to fail.

Non-messenger RNA drugs, such as RNAi, siRNA and other oligonucleotides, are also known and can also be formed into lipid nanoparticle compositions (RNA-LNP). RNA-LNP drugs can be chemically modified to improve their stability and shelf life at room temperature (such chemical modification is not possible for mRNA-LNP technology which requires interaction with cellular proteins to function appropriately). Chemical modification of RNA-LNP can be difficult and expensive to achieve but is nonetheless often preferred to avoid the significant distribution costs associated with non-modified RNA-LNP drugs which must similarly be kept at very low temperatures, as well as the difficulty associated with managing drug efficacy over time due to the limited molecular half-life.

In short, the low temperature requirements of mRNA-LNP and RNA-LNP drugs present a major challenge for their distribution and development.

Other problems associated with known systems for producing nanoparticle compositions include limited scalability, usability, and/or reliability. Repeat agitation of the bulk RNA and lipid fluid mixture using pipettes or syringes is known to lead to formation of mRNA-LNP (or RNA-LNP). However, such systems are often difficult to use effectively, consistently and efficiently. Reliably, scalably, and efficiently obtaining lipid nanoparticle compositions of mRNA and RNA remains a challenge.

SUMMARY

One general aspect of this invention is directed to an adapter. The adapter includes a first port configured to connect with a first container; a second port configured to connect with a second container; and a third port configured to connect with a third container. The adapter further may include a mixing channel extending from a first end in fluid communication with the third port to a second end, and the mixing channel may include a tortuous path along a longitudinal axis of the adapter.

Implementations of the adapter may include one or more of the following features. The adapter where the mixing channel is a microfluidic channel. The mixing channel may include dimples. The mixing channel may include a pathway that is cylindrically-shaped, and the dimples extend radially outwardly beyond the pathway into a body of the adapter. The tortuous path extends into and out of the dimples and the pathway along the longitudinal axis. The dimples surround the pathway. The dimples are arranged in sets of dimples that extend along the longitudinal axis. Each set of the sets of dimples includes two circumferential rows of dimples that are angularly offset relative to each other about the longitudinal axis of the adapter. The mixing channel has an inner dimension of between 20-200 μm. The mixing channel may include a constriction, where the constriction is a portion of the mixing channel having an inner dimension that is smaller than a preceding and/or a succeeding portion of the mixing channel. The adapter may include a first transit channel that connects the first port with the mixing channel and a second transit channel that connects the second port with the mixing channel. The tortuous path is configured to induce localized changes in a direction of flow of liquid moving through the mixing channel. The adapter may include a one-way valve connected to the second port. The third port is configured to be in bidirectional fluid communication with the third container. The third port may include at least one of a rubber diaphragm configured to be pierced by a needle or a fitting configured to affix the third container to the third port, where the fitting is optionally a Luer taper fitting. The mixing channel may include at least one turn between sequentially connected channel portions, and an angle between sequentially connected substantially straight channel portions is at least one of less than 120 degrees, less than 100 degrees, 90 degrees, or less than 90 degrees. The at least one turn may include one of a square junction between the sequentially connected channel portions, a triangular junction between the sequentially connected channel portions, or a sawtooth junction between the sequentially connected channel portions. The at least one turn may include at least one of 2 turns, 4 turn, 10 turns, or more than 10 turns. The mixing channel may include 40 turns or less. The adapter may include a plurality of mixing channels, and where each mixing channel connects the first and second transit channels to the third port. The adapter may include a further first transit channel and a further second transit channel, the further first and further second transit channels are connected with the third port via the mixing channel. The third container is a syringe. The first container and the second container are fixed-volume containers. The first container holds an organic compound in at least 25% alcohol, where the organic compound is optionally a lipid. The second container holds a dehydrated lyophilized RNA. The first container and the second container are removably connected to the first port and the second port respectively. The third container is a syringe connected to the third port, where the syringe holds a buffer.

Another general aspect of the disclosure includes a method of mixing two constituents of a pharmaceutical complex via an adapter. The adapter includes a first port connected to a first container holding a first constituent of the two constituents; a second port connected to a second container holding a second constituent of the two constituents; a third port configured to connect to a syringe; a mixing channel extending from a first end in fluid communication with the third port to a second end; a first transit channel that connects the first port with the mixing channel; a second transit channel that connects the second port with the mixing channel, where the mixing channel may include a tortuous path along a longitudinal axis of the adapter. The method includes connecting the syringe, which may include a plunger, to the third port, and withdrawing the plunger. Withdrawing the plunger draws the first constituent from the first container into the first transit channel and the second constituent from the second container into the second transit channel. Withdrawing the plunger further draws the first and second constituent into the syringe via the mixing channel.

Implementations may include one or more of the following features. The method where the first constituent is an organic compound in at least 25% alcohol solution and the second constituent is a dehydrated pharmaceutical composition. Depressing the plunger transfers at least a portion of the aqueous buffer into the second container. The method may include, prior to connecting the syringe to the third port, connecting the first container to the first port, and connecting the second container to the second port.

Another general aspects of the disclosure includes a method of manufacturing an adapter. The method includes forming a first depression in a first polymer piece. The method also includes fusing the first polymer piece to a second polymer piece such that the first depression defines a mixing channel extending from a first end to a second end. The mixing channel may include a tortuous path along a longitudinal axis of the adapter.

Implementations may include one or more of the following features. The method of manufacturing where the first depression may include a first discontinuous depression. The method further may include fashioning a second discontinuous depression in the second polymer piece. Fusing the first polymer piece to the second polymer piece may include offsetting the first discontinuous depression and the second discontinuous depression such that the second discontinuous depression defines the mixing channel. The method of manufacturing may include offsetting the first polymer piece and the second polymer pieces by 100 to 200 μm. The first and second discontinuous depressions are formed by injection or compression molding.

BRIEF DESCRIPTION OF THE DRAWINGS

Specific embodiments of the present disclosure are described below in the detailed description by way of example only and with reference to the accompanying drawings, in which:

FIG. 11A illustrates a top down view of the adapter of FIG. 10;

FIG. 11B illustrates a cross section view of the adapter of FIG. 11A; and

Like reference numerals are used for like components throughout the drawings.

DETAILED DESCRIPTION

Figure 1A:
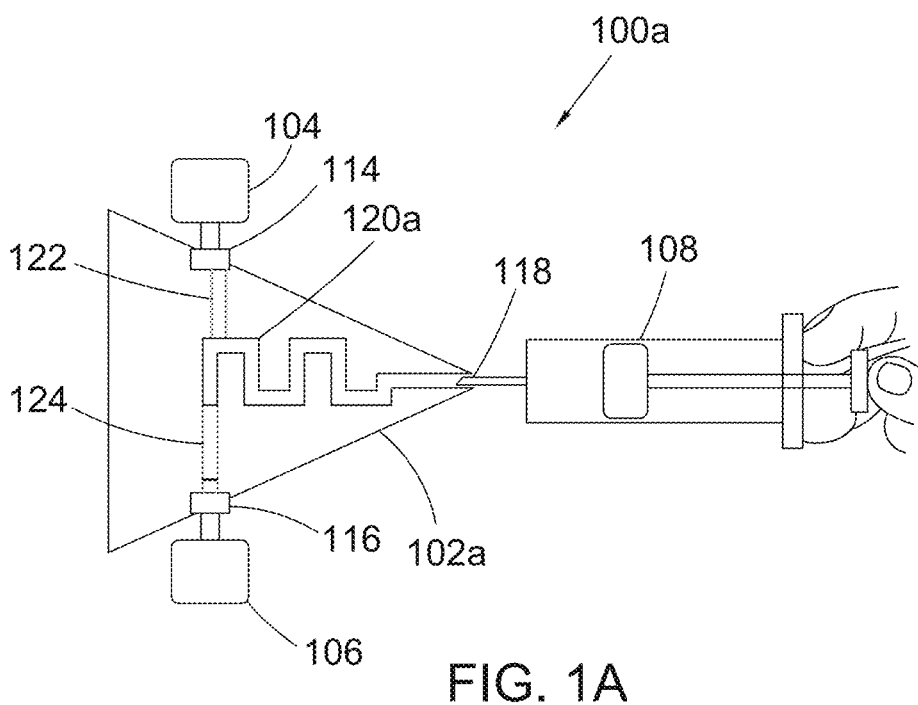
FIG. 1A illustrates a cross-sectional view of an example system according to the disclosure.
Figure 1B:
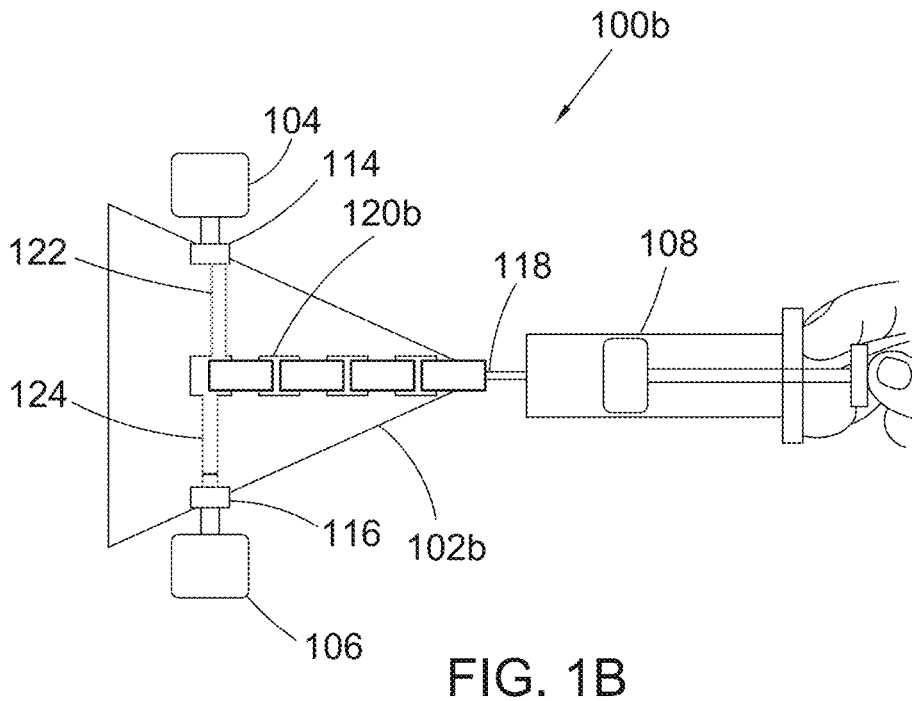
FIG. 1B illustrates a cross-sectional view of another example system according to the disclosure.

FIG. 1A depicts a system 100a for mixing the contents of two containers 104, 106 by way of an adapter 102a and a container 108 (e.g., a syringe). FIG. 1B depicts a system 100b for mixing the contents of the two containers 104, 106 by way of another adapter 102b and the container 108.

FIG. 1A shows an adapter 102a which is connected to a first container 104, a second container 106, and a third container 108. A container 104, 106 and/or a third container 108 can be connected to the adapter 102a when the container and/or syringe is in fluid communication with the adapter 102a. The adapter 102a further includes a mixing channel 120a having a first end in fluid communication with the third container 108, and a second end in fluid communication with the first container 104 and the second container 106.

The adapter 102a of FIG. 1A can be formed of two pieces 110a and 112a fused together, each of which can be a polymer piece or a glass piece. Alternatively, the adapter 102a can be formed in a single, unitary piece for example via injection molding or 3D printing. To increase the ease with which the fluid to be mixed flows through the adapter, low surface energy materials can be used for at least a portion of the adapter. For example, the pieces 110a and 112a can be formed of or coated by a low surface energy material such as ethylene tetrafluoroethylene (ETFE). Other low surface energy materials may also be used, for example fluoropolymer materials other than ETFE. Alternatively, the surface of the pieces 110a, 112a that form the inner surface of the mixing channel can be treated to reduce the surface energy of the walls of the mixing channel. Although a low surface energy material may provide additional advantages in some embodiments, it is an optional feature of the present disclosure.

Figure 1D:
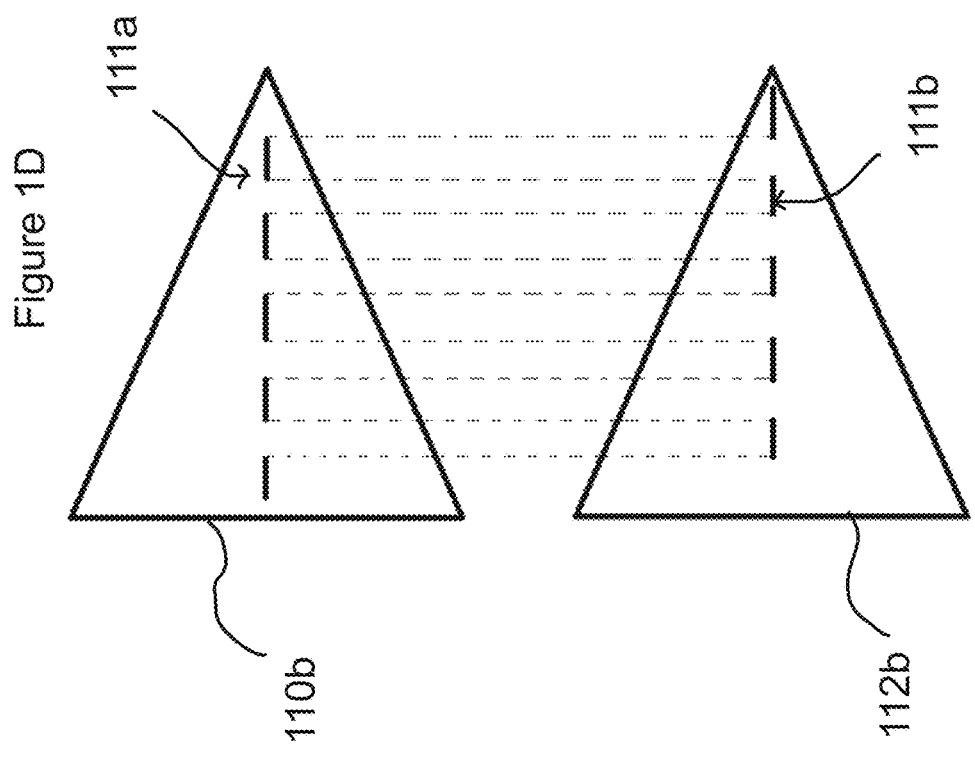
FIG. 1D shows how the mixing channel of FIG. 1B is formed according to a second method.
Figure 1C:
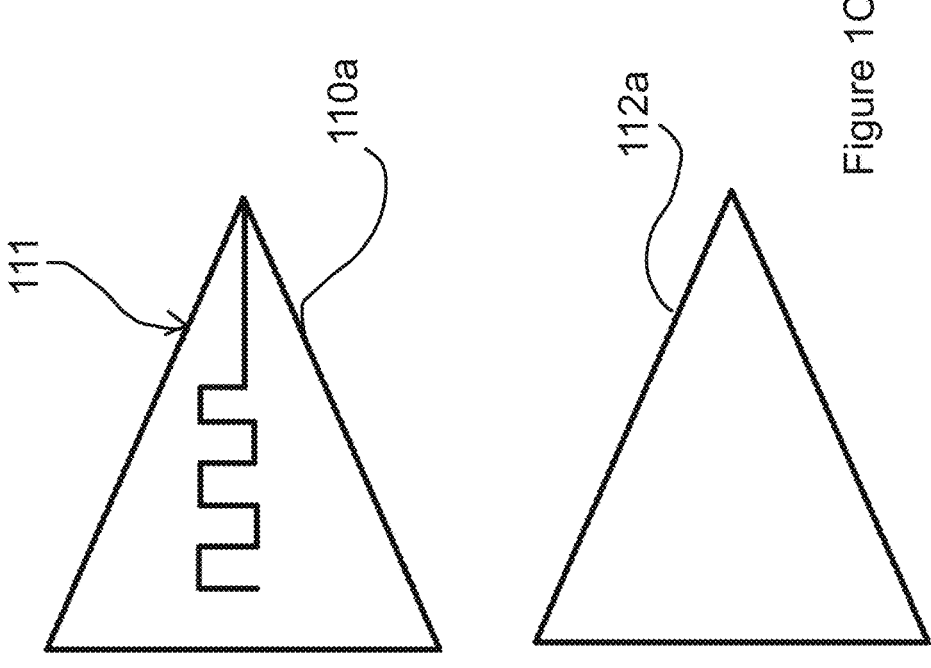
FIG. 1C shows how the mixing channel of FIG. 1A is formed according to a first method.

In the adapter 102a of FIG. 1A, the mixing channel 120a can be defined by a depression formed (by, for instance, molding or engraving) in one or both of the pieces 110a and 112a. FIG. 1C depicts an arrangement in which the mixing channel is formed by creating a depression 111 in one of the pieces 110a, 112a. This arrangement can be used to form the system shown in FIG. 1A. As shown in FIG. 1C, the depression 111 can be formed in just one of the pieces 110a, 112a. The depression 111 here takes the form of an open channel in piece 110a. The other of the pieces (here 112a) does not comprise a channel. Instead, the piece 112a comprises a substantially planar surface, which, when piece 112a is stacked and sealed (or fused) to piece 110a, closes the open channel to form the mixing channel shown in FIG. 1A. The depression can be shaped as a channel as shown in any one of FIGS. 2A to 2D.

FIG. 1B shows an embodiments of the 102b, which is connected to a first container 104, second container 106, and third container 108. As with the adapter 102a of FIG. 1A, adapter 102b includes a mixing channel 120b (shown schematically) having a first end in fluid communication with the third container 108b, and a second end in fluid communication with the first container 104 and the second container 106.

The adapter of FIG. 1B 102b can also be formed of two pieces 110b and 112b fused together, each of which can be a polymer piece, or a glass piece. However, in contrast to the adapter 102a of FIG. 1A, the mixing channel 120b can be defined by a series of depressions in each of the pieces 110b and 112b (fashioned by, for instance, molding or engraving), and offset from each other such that, when the two pieces 110b and 112b are fused, a continuous fluidic path is formed to comprise the mixing channel. In embodiments, the depressions can be discontinuous. Additionally, or alternatively, some or all of the depressions can be formed in a continuous pattern. FIG. 1D depicts an arrangement in which the mixing channel is formed by creating a discontinuous depression 111a, 111b in each of the pieces 110b, 112b.

Figures 2A, 2B, 2C, 2D, 2E:
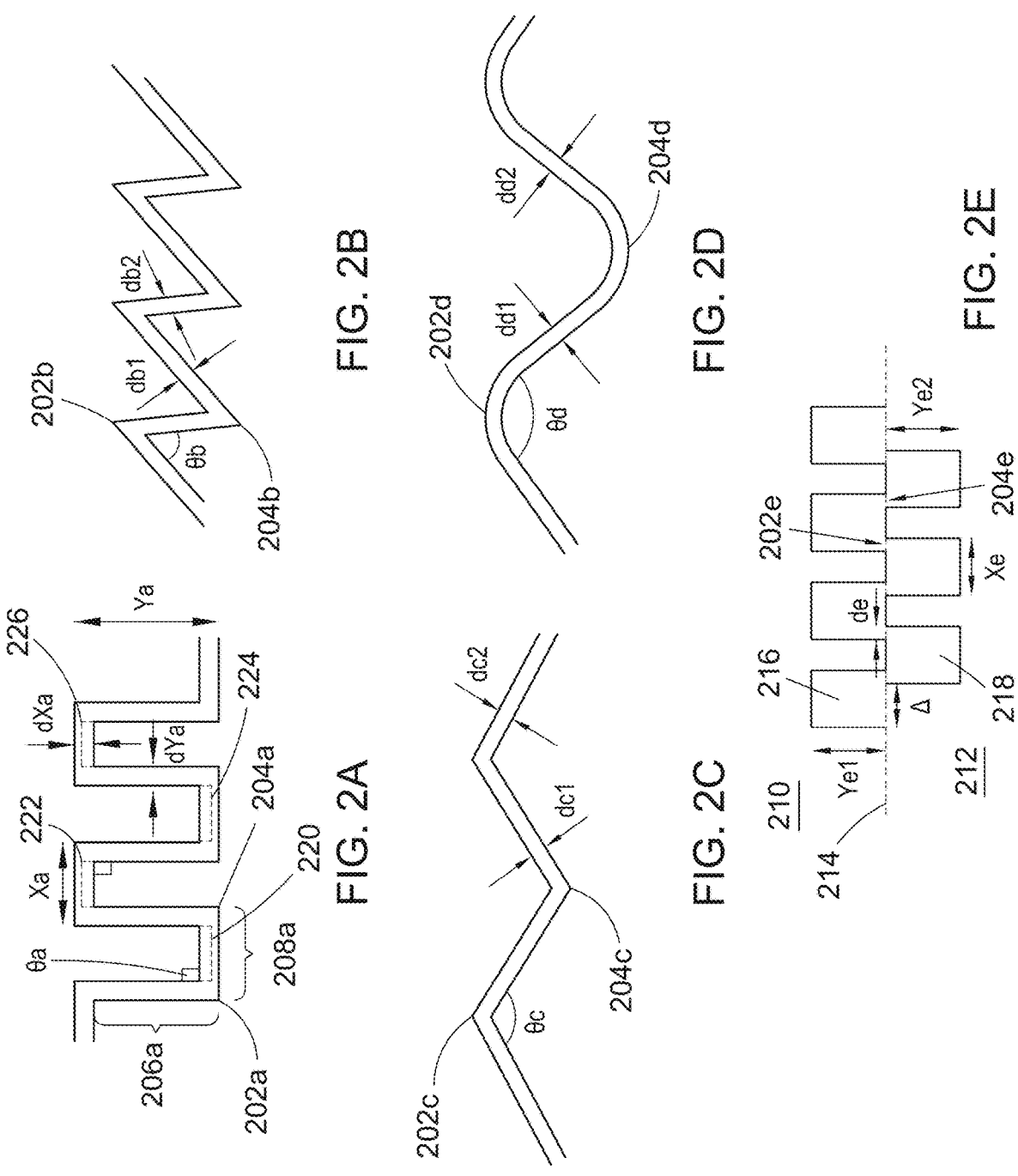
FIG. 2A illustrates a first example of a mixing channel from an adapter according to FIG. 1A or 1B.
FIG. 2B illustrates a second example of a mixing channel from an adapter according to FIG. 1A or 1B.
FIG. 2C illustrates a third example of a mixing channel from an adapter according to FIG. 1A or 1B.
FIG. 2D illustrates a fourth example of a mixing channel from an adapter according to FIG. 1A or 1B.
FIG. 2E illustrates a fifth example of a mixing channel, from an adapter according to FIG. 1B.

As shown in FIG. 1D, the depression can comprise a series of discontinuous depressions or grooves, which form a broken open channel on each of the pieces 110b, 112b. Each of the broken channel segments can be offset from, but overlapping with, the corresponding broken channel segments on the other piece. In this manner, when the first and second pieces are joined together, the discontinuous channel segments on each of the first and second pieces 110b, 112b are in fluid communication with each other to form a tortuous mixing channel, as shown in FIG. 1B. Tortuous, as used herein, can include the plain and ordinary meaning and can be used to describe pathways that themselves change direction or mixing channels that include features (e.g., dimples of FIG. 2F) that deviate off of a pathway to cause some or all of a fluid to change direction. Examples of such offset depressions are shown in FIG. 2E, which will be explained in more detail later.

Figure 1F:
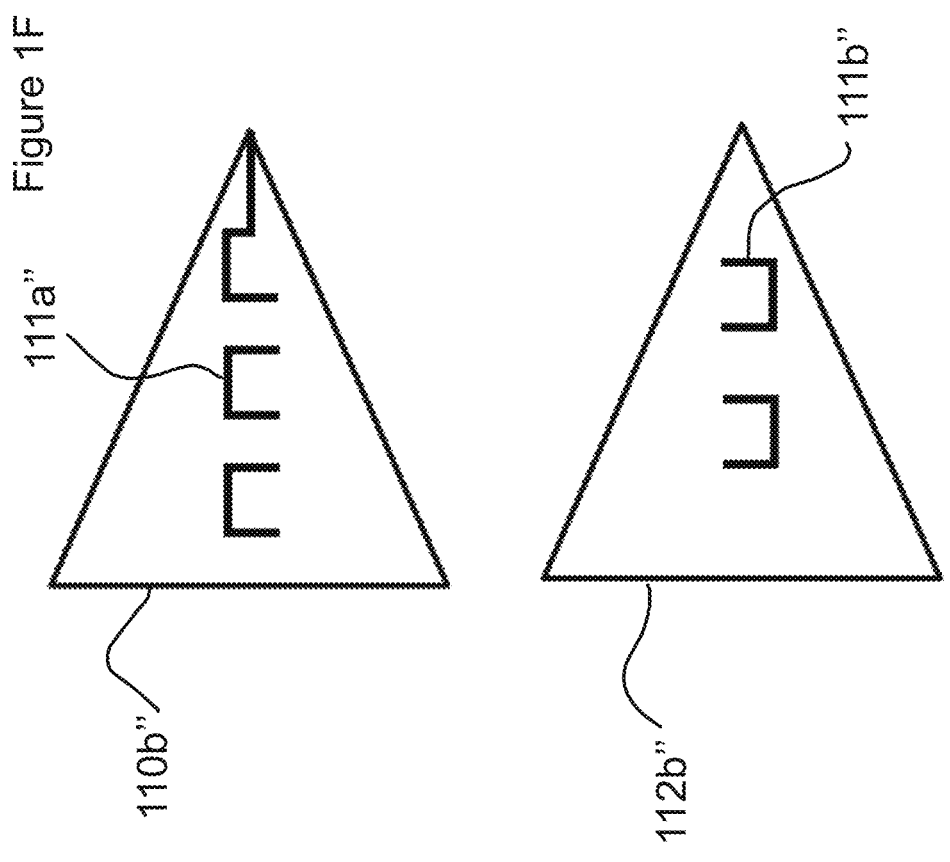
FIG. 1F shows yet another method of forming a mixing channel according to the disclosure.
Figure 1E:
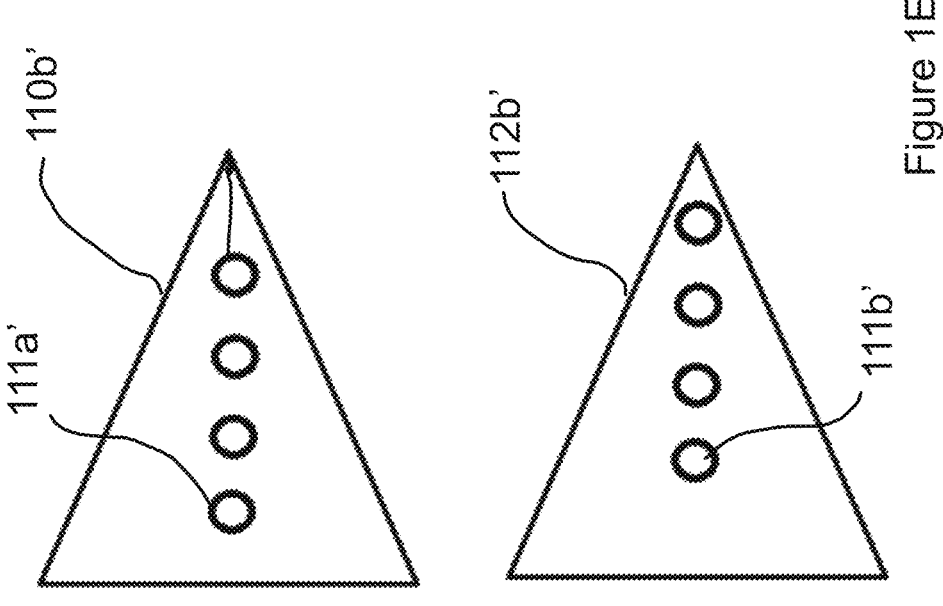
FIG. 1E shows another method of forming a mixing channel according to the disclosure.

Two further methods of forming an adapter from first and second pieces are illustrated schematically in FIGS. 1E and 1F.

The arrangement shown in FIG. 1E is similar to the arrangement shown in FIG. 1D, in that a discontinuous depression 111a' is formed in the first piece 110b' and a second discontinuous depression 111b' is formed in the second piece 112b'. Rather than a broken channel (as shown in FIG. 1D), the arrangement of FIG. 1D comprises a plurality of adjacent but spaced recesses. The recesses in the first piece are offset from the recesses in the second piece such that when the pieces are sealed together, the recesses in the first piece overlap with the recesses in the second piece to form continuous fluid communication through a channel formed in the completed adapter.

The arrangement shown in FIG. 1F differs from the arrangement shown in FIGS. 1C-1E. In the arrangement shown in FIG. 1F, discontinuous depressions 111a" and 111b" are formed in each of the pieces 110b" and 112b". However, the discontinuous depressions are each in the form of a square or U-shaped channel segments, having closed ends. The segments are offset from each other such that when the first and second pieces are sealed together, the channel segments on opposing pieces are in fluid communication with each other, thus forming a tortuous path through the adapter. Note in the embodiment shown in FIG. 1F, the fluid flow path extends in 2 planes, with the U-shaped segments providing a channel segment extending in first plane, and the overlapping portions of the segments providing a stretch of mixing channel that extends in a second plane, orthogonal to the first plane. This may further improve mixing by providing a more tortuous path for the fluid to move along as it travels through the mixing channel.

Although FIGS. 1C to 1F show adapter constructions in which two pieces are sealed together in an opposition relationship, it will be appreciated that three or more pieces can be used. Moreover, one or both of the pieces can be coated, e.g., with a film, so that at least one (and optionally 2 or more) layers of film are disposed between the first and second pieces. Advantages of applying one or more layers of film may include lowered surface energy within the mixing channel, improved sealing of the first and second pieces, and/or an inert surface for the inner surface of the mixing channel.

The methods of forming the adapters 102a and 102b are discussed in more detail later with reference to FIG. 7.

Returning now to FIGS. 1A and 1B, the functionality of the mixing channel 120b of adapter 102b is substantially the same as the functionality of mixing channel 120a of adapter 102a. In particular, both mixing channels 120a, 120b are arranged to create turbulent flow of a fluid flowing therethrough. Comments regarding mixing capability, function, input, output, and so on apply equally to mixing channel 120*a* and mixing channel 120*b*. The following description refers to adapter 102*a*, but applies equally to adapter 102*b* and should be read as such.

The adapter 102*a* can be configured to connect to a plurality of containers, such as two containers, or more than two containers. Any reference to two containers herein should therefore be construed as including three or more containers. Each container 104, 106 can be a vial which is suitable for storing a medicament or a constituent part of a pharmaceutical complex. For example, the first container 104 may store an RNA component (such as an mRNA component, a siRNA component, a RNAi component or a microRNA component), while the second container 106 may store an alcohol-dissolved (e.g., ethanol-dissolved) lipid component to be mixed with the RNA component. Any reference to RNA or mRNA herein should be taken to mean any type of RNA, including those outlined above. The containers 104, 106 are connected to the adapter 102*a* at respective container ports 114 and 116 (sometimes referred to herein as first port 114 and second port 116). That is, a first container 104 is connected to first port 114 of the adapter 102*a* and the second container 106 is connected to second port 116 of the adapter 102*a*.

Further, the ports 114, 116 can be configured such that the respective containers 104, 106 are temporarily or removably connectable thereto. For example, one or both of the first port 114 and the second port 116 may comprise screw thread ports, and the corresponding first container 104 and/or second container 106 may comprise complementary screw thread openings such that the respective container can be connected to or placed in fluid communication with the port by engaging the screw thread port with the complementary screw thread opening. It will be appreciated that one or both of the first port 114 and the second port 116 may comprise removable coupling mechanisms such as those described in WO2011/077434. The disclosure of WO2011/077434 is hereby incorporated by reference. As the adapter 102*a*, in some embodiments, can be configured to connect to any number of containers, the adapter may comprise an equal number of ports for connecting to each of the containers accordingly. Furthermore, one or more of the ports may include a one-way valve arranged to allow fluid flow into the adapter, and to restrict or substantially prevent fluid flow out of the adapter. Ports for connecting the adapter to each of the containers are discussed below in more detail with respect to FIG. 3.

Returning to FIG. 1A, container 108 can be any type of medical syringe or may alternatively be any type of reciprocating pump or container suitable for containing a pharmaceutical complex. Container 108 can be connected to adapter 102*a* through a third port 118 of the adapter 102*a* (hereafter "syringe port" or just "port"). In most embodiments, the third port 118 is configured to provide temporary or removable connection between the container 108 and the adapter 102*a* and, in some embodiments, the third port 118 of adapter 102*a* may allow bidirectional fluid communication with the syringe. Example third ports 118 include a rubber diaphragm configured to be pierced by a needle or a Luer lock taper fitting. Third ports are discussed below in more detail with respect to FIG. 4.

With continued reference to FIG. 1A, adapter 102*a* includes a mixing channel 120*a* extending from a first end in fluid communication with the third port 118 to a second end in fluid communication with the first port 114 and the second port 116. In some embodiments, multiple mixing channels can be provided optionally in parallel, each allowing fluid communication from the third port 118 to the first port 114 and the second port 116. Providing multiple mixing channels has the advantage of increasing the overall throughput of the adapter.

Mixing channel 120*a* is configured to promote mixing of fluids flowing through the mixing channel by inducing turbulence within such fluids. Mixing channel 120*a* comprises a tortuous path. The tortuous path can include, for example, baffles, turns, bends, depressions, dimples, or combinations thereof for generating turbulent fluid flow through the channel. FIGS. 2A-E depict geometries, dimensions, configurations and functionalities of example mixing channels.

With reference to FIG. 1A, mixing channel 120*a* may not be in direct fluid communication with the first port 114 or the second port 116. Rather, mixing channel 120*a* can be in fluid communication with the first port 114 and the second port 116 via a first transit channel 122 and a second transit channel 124, respectively. That is, the first transit channel 122 may extend from the second end of the mixing channel 120*a* to the first port 114, and the second transit channel 124 may extend from the second end of the mixing channel 120*a* to the second port 116. Transit channels are discussed in more detail below with respect to FIG. 3.

A possible use of the system 100*a* of FIG. 1A and the system 100*b* of FIG. 1B is for the mixing of constituents of a pharmaceutical complex for formation of that pharmaceutical complex. Here, the constituents can be in a shelf-stable state and provided within separate respective containers 104, 106. Embodiments of the adapters 102*a* and 102*b* have two connector ports 114 and 116 and are therefore suitable for the mixing of two such constituents. It will be appreciated that if more than two constituents are to be mixed then more than two containers can be provided, each of which may contain at least one constituent. An adapter having more than two container ports may similarly be used in such situations. Further, any number of constituents can be provided in an unmixed state within a single container.

In order to mix the constituent components, the first container 104 and the second container 106 are respectively connected to the first port 114 and second port 116, and a container 108 (e.g., a syringe) is connected to the third port 118. In embodiments in which the container 108 is a syringe, a plunger of the syringe can be withdrawn to induce a pressure differential at the orifice of the container 108. This pressure differential extends from the orifice of the third container 108 at the first end of the mixing channel 120*a* to the second end of the mixing channel 120*a* to which the first container 104 and the second container 106 are fluidly connected. Consequently, as the plunger is withdrawn, the constituents are drawn out of the first container 104 and the second container 106 and pass through the respective first and second transit channels 122, 124 (if present), into the mixing channel 120*a*, through the mixing channel to the third port 118, and into the third container 108. As the constituents collectively pass through the tortuous mixing channel, turbulence is induced in the fluid flow, and the constituents therefore transition from an unmixed state to a mixed state. The pharmaceutical complex is thereby formed by the constituents collectively passing through the mixing channel 120*a*.

In some embodiments at least one of the constituents can be contained within a container in a storage state, such as a lyophilized, solid, or otherwise stable state suitable for medium-term or long-term storage. The constituent can then be reconstituted from the storage state to a prepared state by, prior to connecting the third container 108 to the third port 118, filling the third container 108 with a reconstituting agent (such as an aqueous buffer or a neutralizing agent) and, prior to withdrawing the plunger of the third container 108 as described above, depressing the plunger of the syringe to transfer the reconstituting agent to the container containing the constituent(s) in the storage state. Accordingly, the components in the storage state are reconstituted by the reconstituting agent and the prepared state of the constituent is therefore achieved. A prepared state is one in which the constituents become mixable in the mixing channel or otherwise end-useable within the pharmaceutical complex. In these embodiments, the port(s) which are not connected to the container(s) comprising the constituent(s) in the storage state may include a one-way valve configured to prevent the reconstituting agent from passing through the port when the plunger of the syringe is depressed.

Next, the plunger of the syringe (i.e., the third container 108) can be withdrawn to draw the prepared state constituents from the first container 104 and the second container 106 respectively into the mixing channel 120*a*, 120*b*, through the mixing channel 120*a*, 120*b*, and into the third container 108. Turbulence is induced within the mixture as the prepared state constituents pass through the mixing channel, which may have the effect of transitioning the solution from a mixture of the constituents into the pharmaceutical complex. In alternative embodiments, the first container 104 and the second container 106 can be syringes, where one of which includes the prepared-state constituent. Mixing can be induced within the mixing channel 120*a*, 120*b* in a similar manner but the force driving the fluid can come from simultaneously depressing the plungers of the syringes forming the first container 104 and the second container 106.

Accordingly, systems 100*a* and 100*b* of FIGS. 1A and 1B can be used to form a ready-to-inject RNA-LNP (for instance, mRNA-LNP) complex by mixing the constituents of RNA and lipid dissolved in ethanol via the above outlined method. Here, the RNA is provided within the first container 104 in either a storage state (for instance, as lyophilized RNA or mRNA, or RNA or mRNA in a solution, for example an aqueous solution) or a prepared state, and the ethanol-dissolved lipid is provided within the second container 106.

Example methods of using the adapter 102*a* are described in more detail below with respect to FIGS. 5, 6A and 6B.

FIGS. 2A-2E depict example embodiments of the adapter's mixing channel in profile according to examples of the present disclosure. The mixing channels of FIGS. 2A-2D comprise a tortuous path which, positioned within the adapter 102*a* of FIG. 1A and, meanders in a plane parallel to the interface plane between the first piece 110*a* and the second piece 112*a*. The mixing channel of FIG. 2E comprises a tortuous path which, positioned within the adapter 102*b* of FIG. 1B, meanders in a plane perpendicular to the interface plane between the first piece 110*b* and the second piece 112*b*. The mixing channel of FIG. 2F forms a tortuous path which, positioned within the adapter 102*b* of FIG. 2B, causes fluid to flow into and out of a pathway of the mixing channel 120*b*. The cross-section of the mixing channel (i.e., perpendicular to the view depicted in FIGS. 2A-2E) may take substantially any form, such as circular, square or rectangular.

Each mixing channel comprises a path along which a fluid (typically a liquid) may flow. The path is a tortuous path comprising many bends, 202*a*, 204*a*, 202*b*, 204*b*, 202*c*, 204*c*, 202*d*, 204*d*, 202*e*, 204*e*. As the fluid passes through a bend, localized changes are induced in the fluid flow directions. Accordingly, as the fluid passes through the bend, the degree of turbulence (i.e., the Reynolds number) of the fluid flow is increased. As the degree of turbulence is increased, the parallelism of the components of fluid flow is reduced and therefore, the degree of mixing can be increased. Consequently, increasing the turbulence of the fluid in the mixing channel can promote mixing of the components of that fluid.

The degree by which turbulence of the fluid flow is increased across a single bend is dependent on the geometry of the bend. As such, the geometry of the bend can be chosen depending on the degree of turbulence required to achieve the required amount of mixing for any given application of the adapter. Sharp bends (defined herein as bends including a discontinuity in their gradient that forms a vertex, or a small radius of curvature—e.g., in the same order or magnitude of the channel width—or a large height change over projected distance), like those depicted in FIGS. 2A-C and 2E) cause a greater increase in turbulence than smooth bends (such as bends with continuous gradients like those depicted in FIG. 2D). As such, the sharper the bend, the greater the increase in turbulence across the bend and the smoother the bend, the lesser the increase in turbulence across the bend. In one configuration, the bend between adjacent channel portions can be 90 degrees over 10 μm or less. Similarly, the angle of the bend (i.e., the angle between sequentially connected substantially straight channel portions) affects the increase in turbulence across the bend, where lower angle bends (such as the 90-degree junctions 202*a*, 204*a* or acute angle junctions 202*b*, 204*b* depicted in FIGS. 2A and 2B) may more effectively promote turbulence than higher angle bends (such as the obtuse angle bends of junctions 202*c*, 204*c*, 202*d* and 204*d* depicted in FIGS. 2C and 2D). A channel portion can be said to be substantially straight when it has close to zero curvature.

Accordingly, sharper and/or tighter-angled bends can be chosen for applications where a higher degree of turbulence is required to achieve desired mixing (for example where lipid nanostructures are to be formed). Equally, blunter and/or looser-angled bends can be chosen for applications where a low degree of turbulence is required to achieve desired mixing or where a lower flow volatility is required to maintain certain physical properties of the constituents during mixing, or chosen for the ease of manufacturing because it is easier to manufacture blunter bends more consistently. Suitable bend angles include any bend angle less than or substantially equal to 120 degrees.

A single bend is unlikely to provide enough of an increase in turbulence to transition fluid flow from a fully laminar state to a fully turbulent state. Put another way, a single bend is unlikely to provide enough of an increase in turbulence to transition the fluid from an unmixed state to a desired mixed state. Therefore, the mixing channel comprises multiple bends, each of which incrementally increases the turbulence of the fluid. This way, the mixing channel as a whole may enable the fluid to transition from an unmixed state to a mixed state by way of many incremental transitions. The higher the number of bends, the higher the degree in mixing across the mixing channel. However, as the number of bends increases, so too does the resistance to fluid flow through the mixing channel. As such, the number of bends can be chosen to provide a desired degree of mixing, whilst avoiding impractically high resistance for use with a manually driven syringe. Considering this, in one implementation the inventors have found that an arrangement of between 10 and 40 bends is particularly useful for producing mRNA-LNP or RNA-LNP compositions. However, as the reader will understand, different numbers of bends can be used in different contexts.

In some embodiments, the sides of the mixing channel comprise or are coated with a low surface energy material, such as a low surface energy polymer or low surface energy glass to ensure low bonding between the fluid in the mixing channel and the sides of the mixing channel. One example of a suitable material for at least the inner walls of the mixing channel is EFTE. Forming the sides of the mixing channels of low surface energy materials can reduce loss of constituents across the mixing channel during use and therefore may enable the adapter to operate more efficiently.

The path of the mixing channel is a microfluidic path to reduce the influence of volumetric forces on the fluid's flow. Moreover, a microfluidic path can be used to increase the velocity of the fluid flowing through the mixing channel (relative to a path with a larger cross-sectional area), which may further improve mixing. The higher the velocity of the fluid through the mixing channel, the higher the amount of turbulence induced and therefore the higher the degree of turbulence induced across the mixing channel. Velocity is additionally dependent on the force at which the plunger of the syringe is withdrawn.

In at least some embodiments, the microfluidic path may comprise one or more constrictions 220, 222, 224, 226 which have a smaller cross-sectional area than the microfluidic channel portions either side (in other words, the preceding and succeeding channel portions). The constrictions increase the velocity of fluid flow therethrough which may further improve the mixing. The microfluid path can comprise one constriction or a plurality of constrictions.

Accordingly, the fluid path may comprise an inner dimension (or, if the mixing channel has a circular cross-sectional area, inner diameter) between 10 μm and 1 millimeter or less, optionally between 200 μm and 800 μm, between 400 μm and 600 μm, between 600 μm and 700 μm, or between 20 μm and 100 μm. At these scales the effect of bends, especially sharp bends, on the turbulence of the fluid can be amplified and mixing is increased as compared to fluid paths with larger inner dimensions.

As mentioned above in relation to FIGS. 1A and 1B, it is envisaged that the adapter 102a, 102b may comprise a plurality of mixing channels. A plurality of mixing channels can be used to increase the fluid capacity, flow rate and throughput of the adapter 102a, 102b as a whole. Each mixing channel in the plurality of mixing channels can be provided in parallel and with substantially the same geometries. Alternatively, each mixing channel may comprise a different geometry or configuration.

As depicted on FIG. 2A, the mixing channel may comprise a sequence of sharp, square (i.e., 90-degree) junctions 202a, 204a between sequentially connected substantially straight channel portions 206a, 208a. Junctions can be considered to be sharp if, for example, they comprise a discontinuous gradient at their bend. Each of the junctions of FIG. 2A is connected at an angle θa, where θa equals or substantially equals 90 degrees.

In the embodiment of FIG. 2A, the sequentially connected substantially straight channel portions 206a, 208a may alternate between transverse and longitudinal portions, having vertical and horizontal orientations with lengths Xa and Ya respectively. The values of Xa and Ya can be substantially equal, or the values may differ. Typically, Xa and/or Ya can be between 100-200 μm and Xa can be shorter than Ya to allow for further turbulent flow to occur as the cross-sectional area of the channel changes. In other embodiments, Ya can be shorter than Xa to achieve a similar effect.

Each of the mixing channels has at least one inner dimension (e.g., an inner cross-sectional diameter or width) and preferably at least two alternating inner dimensions, such that the cross-sectional area of the channel varies along its length. For example, the length Xa may have an inner dimension dXa and the length Ya may have an inner dimension dYa. Preferably, dXa is less than dYa. For example, the inner dimension dXa can be about 50 μm or less and dYa can be about 100 μm or less. dXa and/or dYa can be greater than or equal to 20 μm. By including at least two alternating inner dimensions, the fluid flowing through the mixing channel undergoes repeated acceleration and deceleration, thus inducing further degrees of turbulence across the channel.

As depicted on FIGS. 2B and 2C the mixing channel may comprise a sequence of sharp acute or sharp obtuse junctions 202b, 204b, 202c and 204d between sequentially connected substantially straight channel portions. In these embodiments the sequentially connected substantially straight channel portions may comprise the same or substantially the same dimensions as Xa and Ya discussed above.

As depicted, the embodiment of FIG. 2B has sawtooth junctions 202b, 204b between the sequentially connected substantially straight channel portions. Each of these junctions connects sequential substantially straight channel portions at an angle θb, where θb is less than 90 degrees.

As depicted, the embodiment of FIG. 2C has triangular junctions 202c, 204c between the associated sequentially connected substantially straight channel portions. Each of these junctions connects sequential substantially straight channel portions at an angle θc, where θc is greater than 90 degrees and less than 120 degrees.

FIG. 2D depicts an example mixing channel which comprises a sequence of smooth junctions 202d, 204d, as distinct from the sharp junctions of FIGS. 2A-2C. A junction can be considered a smooth junction when, for example, there are substantially no discontinuities in the gradients of the junction (or when the junction is not otherwise considered to be a sharp junction). Each of these smooth junctions connects sequential substantially straight channel portions at an angle θd, where θd can be less than 90 degrees, 90 degrees, or less than 120 degrees.

As with the embodiment depicted in FIG. 2A, the mixing channel of FIGS. 2B-D have at least one inner dimension and preferably at least two alternating inner dimensions, db1 and db2, dc1 and dc2, and dd1 and dd2 respectively. For example, in some embodiments, inner dimensions db1, dc1 and dd1 can be less than or equal to 100 μm, and db2, dc2, dd2 can be greater than or equal to 100 μm.

FIG. 2E depicts an example mixing channel from the adapter of FIG. 1B (however, the adapter of FIG. 1B is not limited thereto). This mixing channel is formed by the fusing of pieces 210 and 212 at interface 214. Piece 210 comprises a series of discontinuous depressions 216 formed in a surface thereof, and piece 212 comprises a series of discontinuous depressions 218 formed in a surface thereof. When the surfaces of the pieces 210 and 212 are bonded to each other the result is a series of fluidly connected internal cavities aligned in an offset manner along the interface 214, as shown in FIG. 2E, thereby forming the mixing channel. Depression 216 has a depth equal or substantially equal to Ye1. Depression 218 has a depth equal or substantially equal to Ye2. Equally, each of the depressions 216 and 218 may have a width equal or substantially equal to Xe, where Xe can be between 100-200 μm. Ye1 and Ye2 can be substantially the same as one another, and can be between 50-100 μm. In other embodiments, the dimensions of Xe, Ye1, and Ye2 can be variable along the length of the mixing channel, e.g., to form a constriction.

In the FIG. 2E embodiment, the fluid path defined by the mixing channel is formed by offsetting each series of discontinuous indentation by offset amount Δ, thereby forming an inner dimension of the mixing channel de. For example, Δ can be between 20-200 μm. In embodiments, depressions 216 and 218 can be rectangularly shaped or can form a herring bone pattern.

Figure 2F:
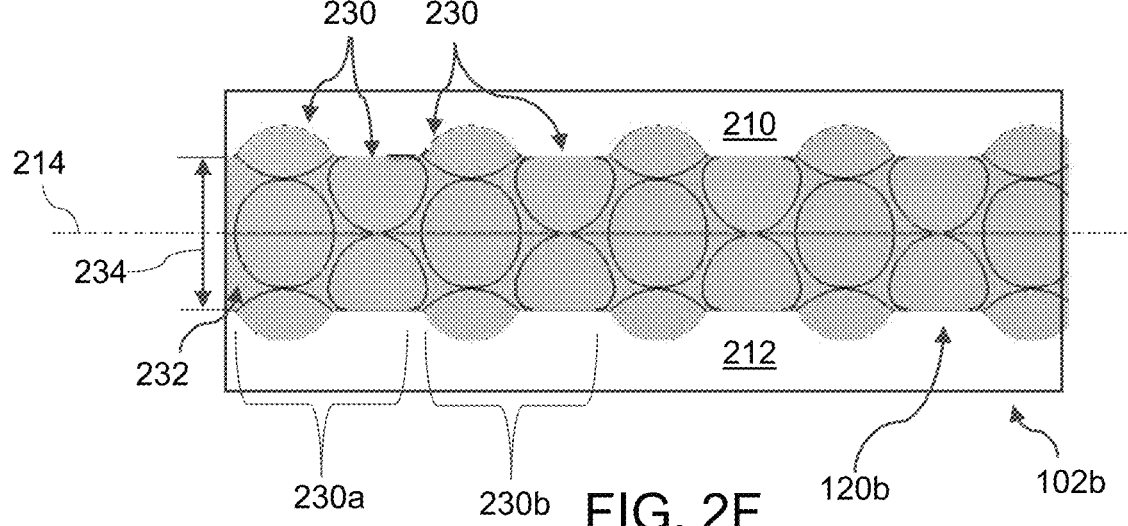
FIG. 2F illustrates a sixth example of a mixing channel, from an adapter according to FIG. 1B.

FIG. 2F depicts an example mixing channel 120b from the adapter 102b of FIG. 1B (however, the adapter of FIG. 1B is not limited thereto). The mixing channel 120b can include a number of dimples 230. The dimples 230 can be formed in a body of the adapter 102b. For example, the dimples 230 can be formed in pieces 210 and 212. The mixing channel 120b can include a pathway 232 extending along a longitudinal axis of the adapter 102b. The pathway 232 can be cylindrically shaped and can have a diameter 234. In embodiments, the diameter 234 can be between 10 μm and 1 millimeter or less, optionally between 200 μm and 800 μm, between 400 μm and 600 μm, between 600 μm and 700 μm, or between 20 μm and 100 μm. Alternatively, the diameter 234 can be 0.3 mm or greater. The diameter 234 can be constant along the longitudinal axis of the adapter 102b, or the diameter 234 can vary along the longitudinal axis of the adapter 102b. The dimples 230 can for example have diameters of less than 400 μm, and optionally between 280 μm and 325 μm. The dimples 230 can deviate off of the pathway 232. The dimples 230 can be recessed into the body of the adapter 102b such that the dimples 230 extend radially outwardly beyond the pathway 232. The dimples 230 can be provided in sets 230a, 230b along the longitudinal axis of the adapter 102b. Each of the sets 230a, 230b can have a length along the longitudinal axis of the adapter 102b of about 700 μm. Each set of the sets 230a, 230b can include at least two circumferential rows of dimples 230 that are angularly offset relative to each other along the longitudinal axis of the adapter 102b.

In embodiments, the dimples 230 can extend radially outwardly beyond the diameter 234 of the pathway 232. Accordingly, to this configuration, fluid flowing through the pathway 232 can follow a tortuous path extending into and out of the dimples 230 and the pathway 232. This fluid obstacle geometry configuration defined by the pathway 232 and dimples 230 can create a purposefully chaotic flow characteristic to mix substances forming the fluid that flows therein. The size, shape, orientation, location, and pattern of this fluid obstacle geometry configuration can be tuned to allow for specific chaotic mixing that yields a predictive pattern of flow. In embodiments, the dimples 230 can be formed along an entire length of the pathway 232. In embodiments, the dimples 230 can be formed surrounding (e.g., above, below, to the sides, circumferentially around, etc.) the pathway 232. According to this configuration, mixing efficiency can be improved.

The mixing channel 120b can be formed by the fusing of pieces 210 and 212 at interface 214. Alternatively, the mixing channel 120b can be formed as a single piece using 3D printing or injection molding, as discussed subsequently herein.

Figure 3:
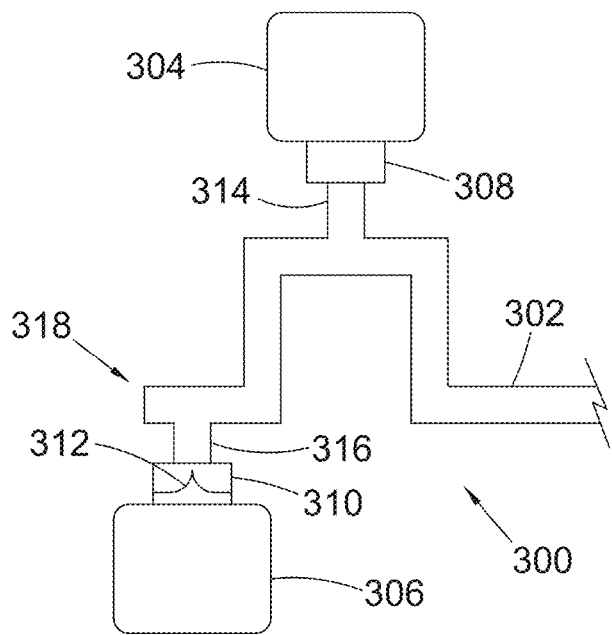
FIG. 3 illustrates a second end of a mixing channel according to any of FIGS. 2A to 2C, as coupled to a first container and a second container according to FIG. 1A or 1B.

FIG. 3 depicts a second end 300 of a mixing channel 302 and, in particular, depicts the connections between the mixing channel 302, the first container 304, and the second container 306. As the reader will understand, any of the mixing channels shown in FIGS. 2A to 2E may have a second end arranged as shown in FIG. 3.

The second end 300 of the mixing channel 302 is fluidly coupled with a first port 308 and with a second port 310. As shown, the first port 308 and/or the second port 310 can be provided offset from the end-most point 318 of the second end 300. Each of the first port 308 and the second port 310 is configured to be connectable with a first container 304 and the second container 306. In this way, each the first port 308 and the second port 310, when connected to the first container 304 and the second container 306 respectively, are configured to provide a conduit between the internal volume of the respective container and the mixing channel 302 of the adapter. As such, the first port 308 and the second port 310 may enable fluid communication to be established between the volumes of the first container 304, the second container 306, and the mixing channel 302 respectively.

The first port 308 and the second port 310 can be permanently attached to the first container 304 and the second container 306, in which case the first container 304 and the second container 306 may comprise an alternative input to enable refill. Alternatively, the first port 308 and the second port 310 can be configured to provide removable or temporary connection with the first container 304 and the second container 306 respectively, enabling the first container 304 and the second container 306 to be externally refillable or replaceable, and/or enabling the adapter to be reusable.

Removable or temporary connection can be provided by structuring the port with any conventional mechanical fastening means. For instance, the first port 308 and the second port 310 may have openings comprising a screw thread along their interior and the openings of the first container 304 and the second container 306 may comprise a complementary screw thread along their exterior. In this way, the screw thread and complementary screw thread can be engaged to connect the first container 304 and the second container 306 to the first port 308 and the second port 310 respectively. As another example, the first port 308 and the second port 310 may removably connect with the first container 304 and the second container 306 by use of a push-on coupling mechanism, where the connection is maintained by friction between the exterior of the openings of the first container 304 and the second container 306 and the interior of the openings of the first port 308 and the second port 310. Preferably the first ports 308 and the second port 310 comprise a vented vial adapter, such as those disclosed in U.S. Pat. No. 8,753,325, in order to draw air into the vials and to ease drawing the fluid through the system. The disclosure of U.S. Pat. No. 8,753,325 is hereby incorporated by reference.

At least one of the ports 308, 310 may further comprise a one-way valve 312. The one-way valve may comprise any suitable valve that permits fluid to flow from the second container 306 to the mixing channel 302 and restricts or substantially prevents fluid from flowing in the opposite direction. A benefit of including one-way valve 312 within at least one port is that a reconstituting agent—as discussed in relation to FIGS. 1A and 1B above and FIGS. 5 and 6A below—can be prevented from entering containers not containing storage state constituents.

Optionally, the second end 300 of the mixing channel 302 may further comprise a first transit channel 314 and a second transit channel 316, extending from the first port 308 and the second port 310 to the mixing channel 302 respectively. Each of the transit channels 314, 316 provides a conduit for fluid communication between the respective port 308, 310 and the mixing channel 302. The first transit channel 314 includes a first end at the first port 308 and a second end fluidly connected to the mixing channel 302. The second transit channel 316 includes a first end at the second port 310 and a second end fluidly connected to the mixing channel 302. In some embodiments the second end of the first transit channel 314 may meet the mixing channel 302 at substantially the same place at which the second end of the second transit channel 316 meets the mixing channel 302. However, in some embodiments (such as that depicted in FIG. 3), the second end of the first transit channel 314 may meet the mixing channel offset from the place at which the second end of the second transit channel 316 meets the mixing channel 302. This offset may span at least one or two bends. Providing such an offset may function to provide a resistance that that reduces the entry of a fluid into the first container 304, e.g., by providing a region of the mixing channel with a hydrophobic surface. The offset additionally can have the benefit of enabling the adapter to be manufactured less intricately and therefore more efficiently and cost effectively.

Figure 4:
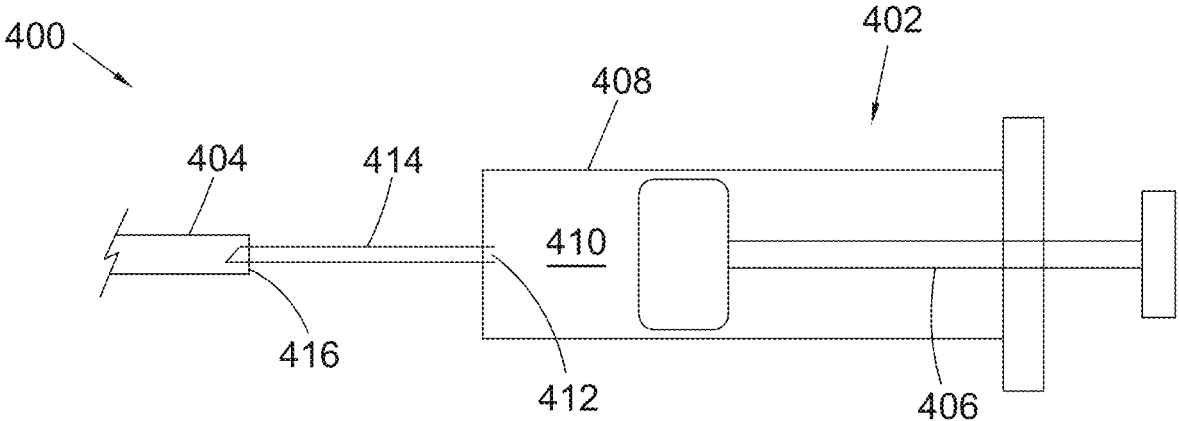
FIG. 4 illustrates a third port of an adapter according to FIG. 1A or 1B, as connected to a syringe.

FIG. 4 illustrates a syringe port 404 to which a syringe 402 is connected.

The syringe 402 can be any conventional type of syringe or reciprocating pump which is suitable for use in a pharmaceutical setting. In particular the syringe includes a plunger 406 (or piston) fitting securely within a barrel 408 and defining a variable internal volume 410 of the syringe. Opposing the plunger, the syringe further comprises an orifice 412 to which a needle 414 can be fitted. Alternatively, the orifice 412 can be included within a Luer lock tip.

The syringe port 404 (or "third port") is configured in any suitable way to provide a connection to a syringe, such that, when a connection is made, the internal volume 410 of the syringe is in fluid communication with the mixing channel via the syringe port 404. In this way, the syringe port may comprise any fitting configured to affix the syringe to the third port. For example, if a needle 414 is attached to the syringe's orifice 412 (as depicted in FIG. 4), the third port may include a rubber diaphragm 416 suitable for repeated piercing by a needle. Alternatively, if the orifice 412 is included within a Luer lock tip, the fitting of the syringe port 404 may include a Luer taper fitting.

This disclosure also includes a method of mixing two constituents of a pharmaceutical complex via any of the adapters disclosed herein. The method comprises connecting a syringe comprising a plunger to the third port and withdrawing the plunger. Withdrawing the plunger causes the first constituent to be drawn from the first container into the first transit channel and the second constituent from the second container into the second transit channel. Withdrawing the plunger further causes the first and second constituent to be drawn into the syringe via the mixing channel.

In this method, the first constituent can be an organic compound in at least 25% alcohol solution and the second constituent is a dehydrated pharmaceutical composition. The syringe may initially hold a reconstituting agent (such as an aqueous buffer), in which case the method further comprises, prior to withdrawing the plunger, depressing the plunger, wherein depressing the plunger transfers at least a portion of the reconstituting agent into the second container.

In some embodiments, the method further comprises, prior to connecting the syringe to a third port of an adapter, connecting the first container to the first port, and connecting the second container to a second port of an adapter.

Figures 5A, 5B:
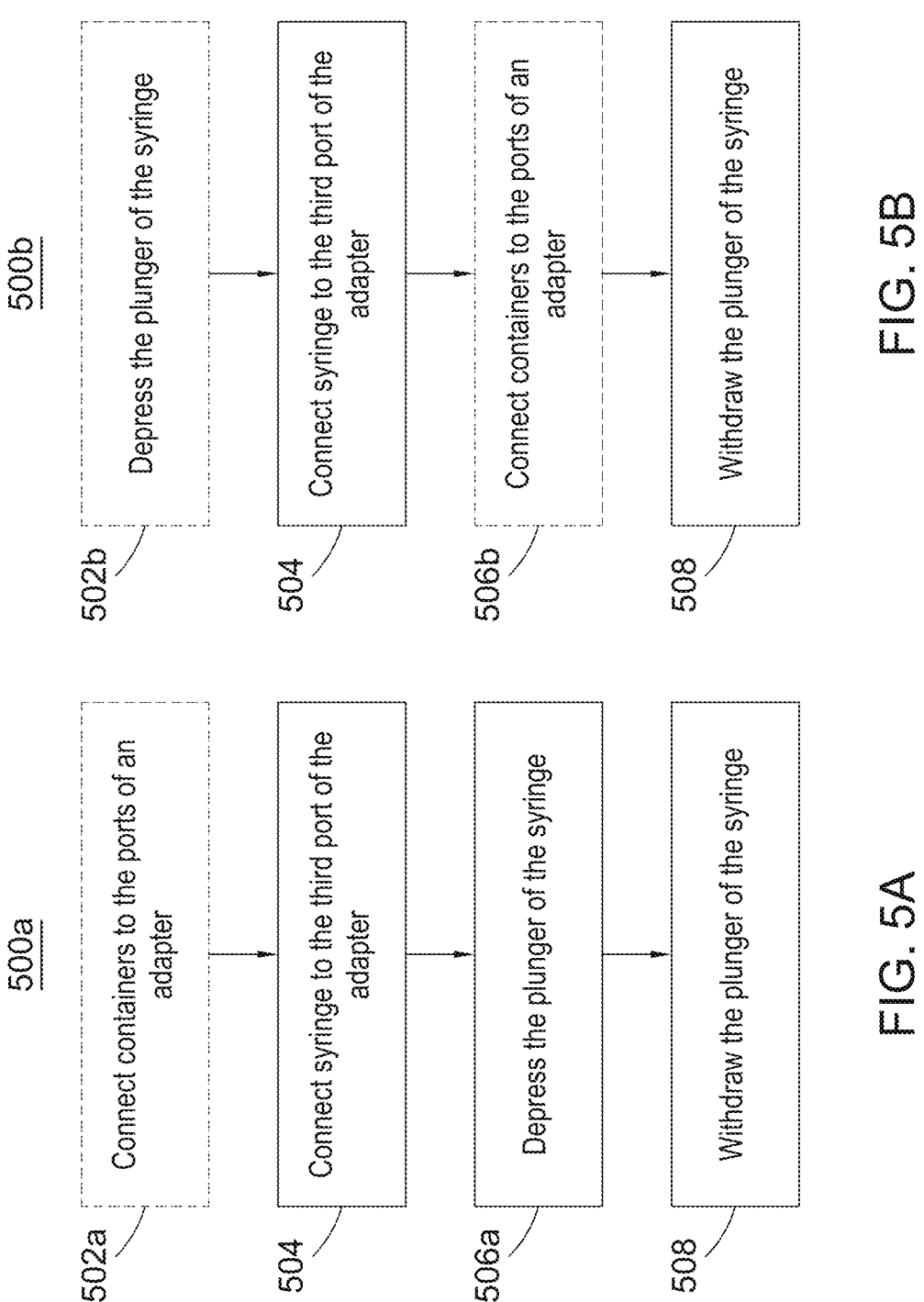
FIG. 5A is a flowchart showing an example method of mixing constituents of a pharmaceutical complex using an adapter according to FIG. 1A or 1B.
FIG. 5B is a flowchart showing another example method of mixing constituents of a pharmaceutical complex using an adapter according to FIG. 1A or 1B.

FIG. 5A depicts a flowchart of an example embodiment of the above outlined method 500a of mixing constituents of a pharmaceutical complex via any of the adapters described herein. FIG. 5B depicts an alternative example embodiment of the above outlined method 500b of mixing constituents of a pharmaceutical complex wherein one of the containers already includes a reconstituted product. Any steps depicted by dashed lines are optional and can be omitted and the ordering of any steps which are not causally related can be changed.

At step 502a, the containers 104, 106 are connected to the ports 114, 116 of an adapter. The containers 104, 106 may contain lyophilized RNA that is not yet reconstituted. This connection can be carried out through any of the methods of connecting containers to ports described herein. Alternatively, the containers may already be provided as connected to the ports of the adapter, in which case this step is omitted.

At step 504, a syringe is connected to the third port (or "syringe port") of the adapter. This connection can be carried out through any of the methods of connecting a syringe to the syringe port described herein. On connection to the adapter, the syringe can be substantially empty, and the plunger of the syringe can be advanced. Alternatively, on connection to the adapter, the internal volume of the syringe may comprise a reconstituting agent (such as an aqueous buffer or a neutralizing agent).

Where the syringe comprises a reconstituting agent, the method 500a of FIG. 5A can be followed and the plunger of the syringe is depressed at step 506a such that the reconstituting agent is impelled through the adapter and into at least one of the containers. If, on connection to the adapter, the syringe is substantially empty, and the plunger of the syringe is pre-depressed (such as, at step 502b), this step can be omitted and the method 500b of FIG. 5B can be followed.

Figure 6A:
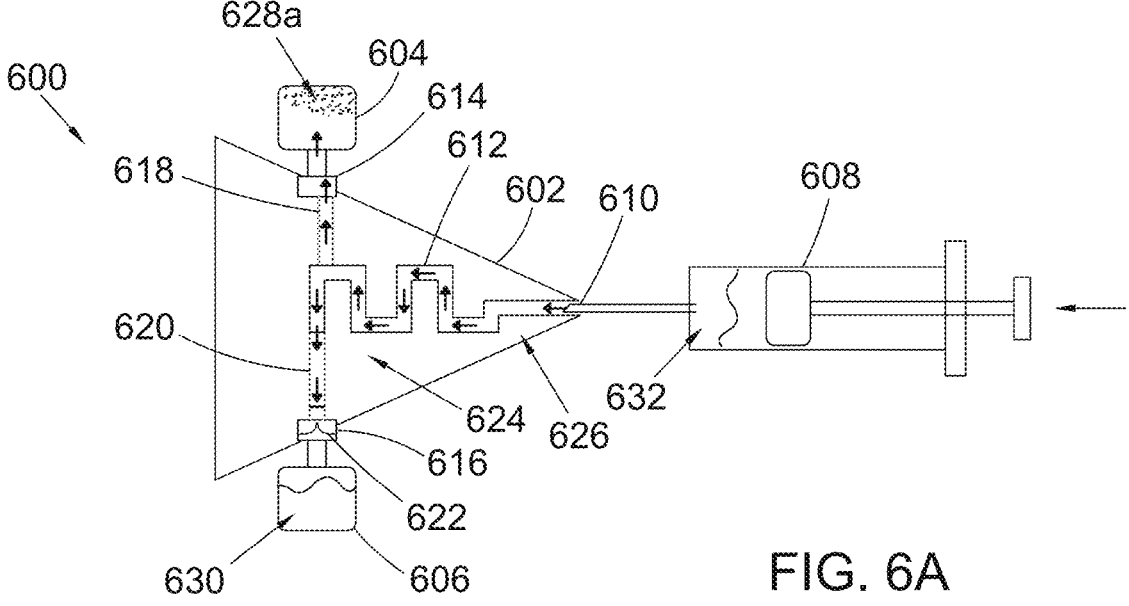
FIG. 6A illustrates an operation of the system of FIG. 1A, responsive to a plunger of the syringe being depressed.

The effect of depressing the plunger at 506a is illustrated in FIG. 6A, which depicts the system 600 comprising an adapter 602 (such as any of the adapters described herein), a first container 604, a second container 606, and a syringe 608. As the plunger of the syringe 608 is depressed, the reconstituting agent 632 flows out of the orifice of the syringe, through the mixing channel 612 along the path defined by the mixing channel, and into the first container 604 containing a first constituent 628a of the pharmaceutical complex in a storage state. The first constituent 628a is then reconstituted within the first container 604 by the reconstituting agent 632.

The second port 616 depicted in FIG. 6A includes a one-way valve 622 oriented such that fluid is inhibited or substantially prevented from passing from the mixing channel 612 to the second container 606. As such, when the reconstituting agent 632 flows to the second port 616, it is prevented from flowing into the second container 606. In alternative embodiments, the one-way valve 622 is not present at the second port, in which case the reconstituting agent 632 is permitted to flow through the second port 616 and into the second container containing constituent(s) 630 of the pharmaceutical context. In these alternative embodiments, the constituent(s) 630 contained within the second container 606 can be configured to withstand dilution by the reconstituting agent 632 by, for instance, being provided in a higher concentration solution than necessary.

At step 508, the plunger of the syringe is withdrawn such that the constituents are drawn from the containers 604, 606 in an unmixed state, through the adapter and into the syringe.

Turbulence induced in the fluid flow by the mixing channel of the adapter results in the constituents being mixed as required upon reaching the syringe. FIG. 5B depicts an alternative scenario where the contents of container 604 may have been reconstituted prior to attachment to the adapter or was never lyophilized. At step 502b, the plunger of the syringe can be depressed to ensure it is ready to withdraw the contents of containers 604, 606 after the syringe is connected to the adapter at step 504. If not already connected to the adapter, the containers 604, 606 can be connected to the adapter at step 506*b*. Finally, the withdrawing of the plunger will be performed at step 508.

Figure 6B:
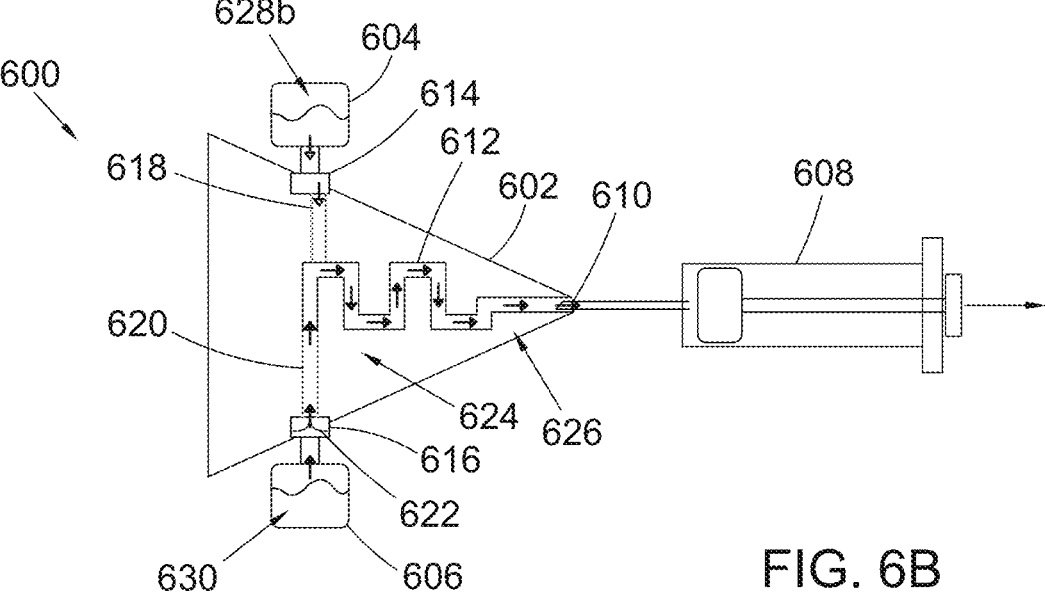
FIG. 6B illustrates an operation of the system of FIG. 1A, responsive to a plunger of the syringe being withdrawn.

The effect of withdrawing the plunger at 508 is illustrated in FIG. 6B, which depicts the same system 600 of FIG. 6A comprising an adapter 602, a first container 604, a second container 606, and a syringe 608. As the plunger of the syringe 608 is withdrawn, a pressure differential is induced across the orifice of the syringe. This pressure differential then propagates through the syringe port 610, through the mixing channel 612 and to the first container 604 via the first port 614 and the first transit channel 618 (if present), and to the second container 606 via the second port 616 and the second transit channel 620 (if present). Consequently, the first constituent 628*b* (here in a prepared state) is drawn from the first container 604 and into the mixing channel 612 (via the first port 614 and the first transit channel 618, if present) at or substantially near the second end 624 of the mixing channel 612. Similarly, the second constituent 630 is drawn from the second container 606 and into the mixing channel 612 (via the second port 616 and the second transit channel 620, if present) at or substantially near the second end 624 of the mixing channel 612.

Then, the first constituent 628*b* and second constituent 630 are drawn from the second end 624 of the mixing channel 612 to the first end 626 of the mixing channel 612 via the mixing channel 612 along the path defined by the mixing channel 612. Here, the mixing channel 612 comprises a number of bends and is configured in any of the ways described with respect to FIGS. 2A-E.

Initially, at the second end 624 of the mixing channel 612, the first constituent 628*b* and the second constituent 630 are in a mutually unmixed state. Then, as the first constituent 628*b* and the second constituent 630 pass through each bend of the mixing channel, the first constituent 628*b* and the second constituent 630 incrementally transition from an unmixed state to an increasingly mixed state, as described with respect to FIGS. 2A-2E.

From the first end 626 of the mixing channel 612, the first constituent 628*b* and the second constituent 630 are then drawn through the syringe port 610 and into the syringe as the pharmaceutical complex. In some embodiments the pharmaceutical complex is drawn into the syringe in a ready-for-use state. In other embodiments, the pharmaceutical complex drawn into the syringe requires further dilution prior to use. In some of these other embodiments, the plunger may not be depressed in its entirety at step 506, in which case some of the reconstituting agent 632 remains within the internal volume of the syringe 608. This reconstituting agent 632 may, within the syringe 608, dilute the pharmaceutical complex such that the result is the pharmaceutical complex within the syringe 608 in a ready-for-use state.

Considering the specific example of forming an mRNA-LNP pharmaceutical complex, a mRNA-LNP (or RNA-LNP) complex can be formed by mixing a first constituent of mRNA (or RNA) in the first container 604 and a second constituent of lipid dissolved in 25% or greater alcoholic solution in the second container 606 via any of the adapters disclosed herein.

In some embodiments, the first constituent comprises pre-prepared mRNA (or RNA) which is in a prepared state, having been reconstituted prior to containment within the first container 604. In these embodiments, a reconstituting agent need not be introduced and step 506 can be omitted from the method 500. Additionally, the one-way valve 622 need not be provided.

In alternate embodiments, the first constituent comprises mRNA (or RNA) in a storage state, requiring reconstitution prior to use. For instance, the mRNA (or RNA) can be lyophilized mRNA (or lyophilized RNA), in which case the reconstituting agent introduced by depressing the plunger of the syringe can be an aqueous buffer. Alternatively, the mRNA (or RNA) can be dissolved in a liquid requiring neutralization prior to use, in which case the reconstituting agent can be a neutralizing agent.

In these alternate embodiments, the one-way valve 622 can be provided, in which case the second constituent (i.e., the lipid dissolved in an alcoholic solution) need not be specially prepared to withstand the neutralizing agent. However, the one-way valve 622 may also be omitted if the second constituent comprises a lipid dissolved in greater than 25% alcoholic solution, preferably between 40-100% alcoholic solution. This concentration can allow the second constituent to withstand dilution by the reconstituting agent without affecting the quality of the resulting mRNA-LNP complex.

Figure 7:
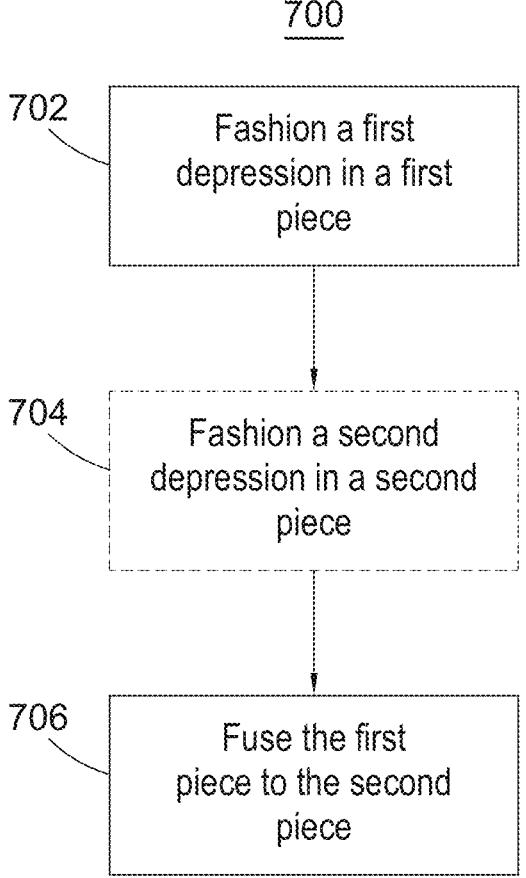
FIG. 7 is flowchart showing an example method of manufacturing an adapter according to FIG. 1A or FIG. 1B.

FIG. 7 depicts a flowchart of an example method 700 of manufacturing an adapter, such as the adapter 102*a* of the system 100*a* of FIG. 1A or the adapter 102*b* of the system 100*b* of FIG. 1B. The step depicted by dashed lines is optional and can be omitted. The method 700 begins by fashioning a first depression in a first piece (e.g., piece 110*a* of FIG. 1A or piece 110*b* of FIG. 1B) at step 702. Next, a second depression can be fashioned in a second piece (e.g., piece 112*a* of FIG. 1A or piece 112*b* of FIG. 1B) at step 704. Finally, the first piece is fused to the second piece at step 706.

The first depression and optional second depression are such that, on fusing the first piece to the second piece, the depressions provide or define a mixing channel 120*a*, 120*b*. On fusing the first piece to the second piece, the depressions may additionally or alternatively provide or define the first transit channel 122 and/or the second transit channel 124. The adapter may additionally be formed with multiple mixing channels in which case more than one first depression and more than one second depression can be fashioned in each of the first piece and the second piece at steps 702 and 704 respectively. Where a plurality of mixing channels is provided, they can be in communication with each other at multiple points along their length so that fluid from one channel may move into fluid from another channel.

In embodiments relating to the adapter of FIG. 1A, each of the first depression and the optional second depression comprises a continuous depression with geometries and configurations such as those described in relation to the mixing channels of any of FIGS. 2A-2D. As such, the mixing channel 120*a* defined by the depressions comprises a tortuous path which winds in a plane parallel the interface plane between the first piece and the second piece. If the first depression in the first piece fashioned at step 702 is sized to equal or substantially equal substantially the whole cross section of the mixing channel, step 704 can be omitted and the second piece can be fused to the first piece without itself comprising a second depression, which can have the benefit of enabling the microfluidic pathway to be formed on a (single) structural piece, for example one which is not also responsible for connection with the syringe or containers, thus simplifying manufacture and reducing costs. Alternatively, step 704 can be included if the first depression fashioned at step 702 is sized to equal or substantially equal a portion (e.g. substantially half) of the whole cross section of the mixing channel, the second depression fashioned at step 704 is sized to equal or substantially equal the remaining portion (e.g. substantially half) of the whole cross section and step 706 involves fusing the first piece to the second piece with the first depression and the second depression aligned.

On the other hand, in embodiments relating to the adapter of FIG. 1B, each of the first depression and the second depression comprises a discontinuous depression, such as a linear array of separated depressions, extending in the direction of the mixing channel 120b. In these embodiments, the fusing of the first piece to the second piece at step 706 includes offsetting the first discontinuous depression from the second discontinuous depression by a chosen amount, such that the first and second discontinuous depressions collectively form the mixing channel when the parts are fused. This is illustrated in FIG. 2E, where part 210b is fused to part 212b, and discontinuous depression 216 is offset from discontinuous depression 218 to form a mixing channel. In one example, the first discontinuous depression and the second discontinuous depression are offset by 20-200 μm. The geometries and configurations of these mixing channels can be any of those described in relation to FIGS. 2A-2D or FIG. 2E, however, in some embodiments relating to FIG. 1B, the mixing channel comprises a tortuous path which winds in a plane parallel to the interface plane between the first piece 110b and the second piece 112b.

Each of the pieces can be formed of substantially any material, preferably a low surface energy material for at least the reasons described above and may comprise a conical shape as depicted in FIGS. 1A and 1B. For example, each of the pieces can be injection or compression molded polymer pieces. Alternatively, each of the pieces can be formed by stamping, etching or laser engraving glass pieces or another substrate. In these scenarios the first depression and/or the second depression can be fashioned in the associated first piece and/or second piece by way of: injection or compression molding; adhering a laser cut polymer film onto an injection or compression molded piece; adhering a micro-molded piece onto an injection or compression molded piece; engraving the depression onto the piece or a portion of the piece over-molded in a polymer adapter; or over-molding a microcapillary in a polymer adapter. Each of these methods of fashioning a depression can beneficially provide a durable adapter with desirable material properties and can scale to industrial volumes effectively and at low cost. Alternatively, the depression(s) on any or each of the pieces can be formed on a film which is laminated on a solid piece to form the enclosed microfluidic pathway. For instance, in the embodiment of FIG. 1B, the film can be a continuously perforated or embossed structure repeating over a 200 μm period. This method can provide a low-cost, low-complexity method for manufacturing the microfluidic pathway.

Either of the first piece and/or the second piece may comprise the structure of the first port 114, second port 116, third port 118 and/or any other components of the adapter. Alternatively, the first port 114, second port 116 and/or third port 118 can be coupled to the first piece and/or the second piece before step 706. Alternatively, the first port 114, second port 116 and/or third port 118 can be coupled to the adapter at the interface between the first piece and the second piece on fusing at step 706.

Figure 8:
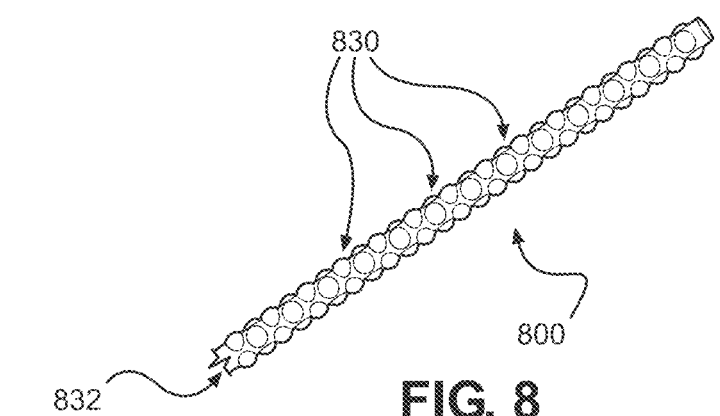
FIG. 8 illustrates an example core pin used to manufacture an adapter according to the disclosure.
Figure 9:
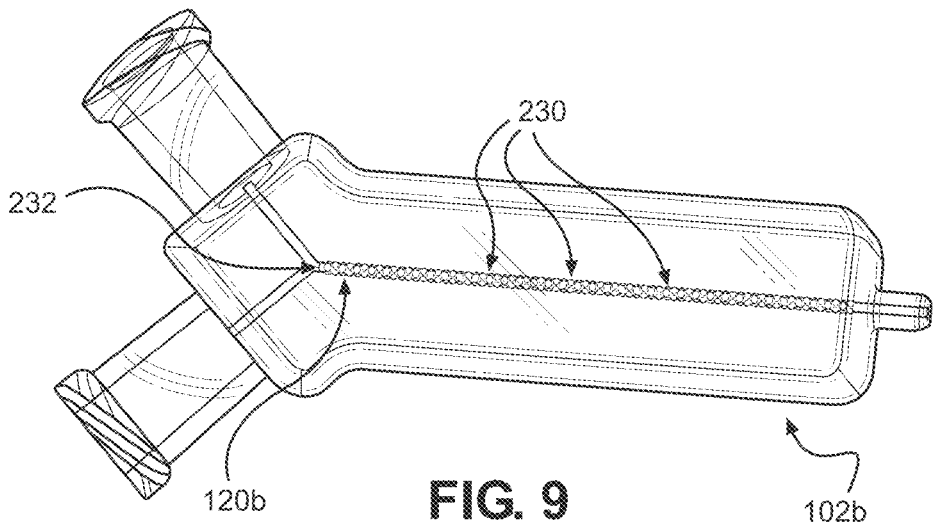
FIG. 9 illustrates an example unitary adapter according to the disclosure.

As discussed above, the mixing channel 120b of the adapter 102b can be formed of a single piece using injection molding or 3D printing. In embodiments, the mixing channel 120b can be formed of a single piece using injection molding, such as liquid silicone rubber injection molding or thermoplastic elastomer injection molding. For example, and as shown in FIG. 8, a core pin 800 can be used in an injection mold to form the mixing channel 120b of FIG. 2F in a single piece of the adapter 102b by injecting liquid (e.g., silicone rubber, thermoplastic elastomer, etc.) into the mold around the core pin 800. The core pin 800 can include a cylindrical rod 832 to form the pathway 232 of the mixing channel 120b. The core pin 800 can include of protrusions 830 extending radially outwardly from the cylindrical rod 832 to form the dimples 230 of the mixing channel 120b. The core pin 800 can be formed of a flexible, resilient material, such as an elastomer, that can deform when the core pin 800 is removed from the molded adapter 102b. The adapter 102b can be released from the core pin 800 (e.g., using a strategically placed air ejector system) and/or the core pin 800 can be extracted from the adapter 102b after molding. Since the core pin 800 is formed of a flexible, resilient material, the core pin 800 can be separated from the molded adapter 102b without damage to the core pin 800 or the adapter 102b. FIG. 9 shows an embodiment of the adapter 102b formed from injection molding that includes a mixing channel 120b formed in a single, integral piece of the adapter 102b and having the dimples 230 and pathway 232 described previously in reference to FIG. 2F.

Figure 10:
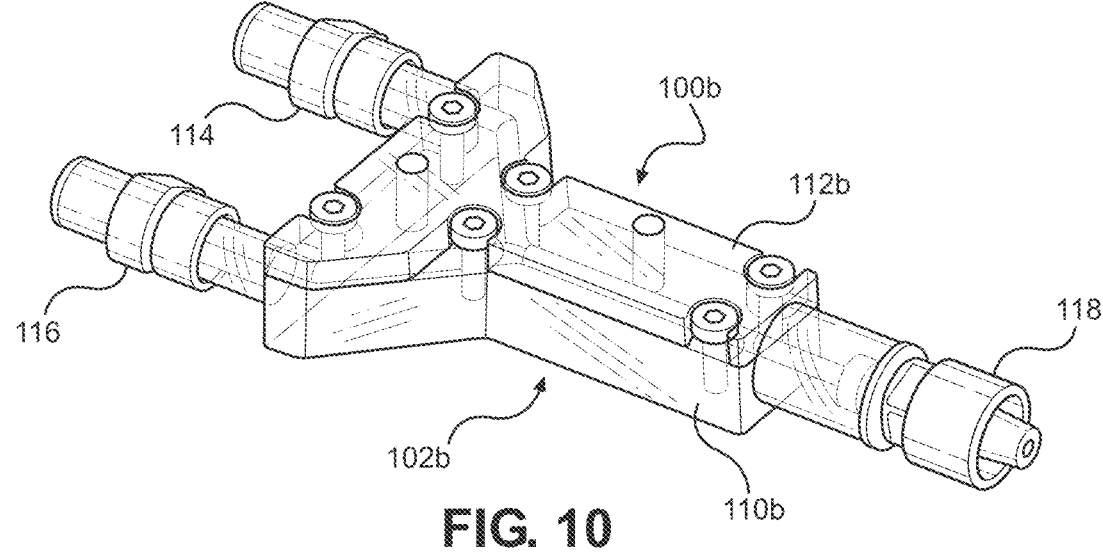
FIG. 10 illustrates a perspective view of an adapter according to the disclosure.
Figure 11C:
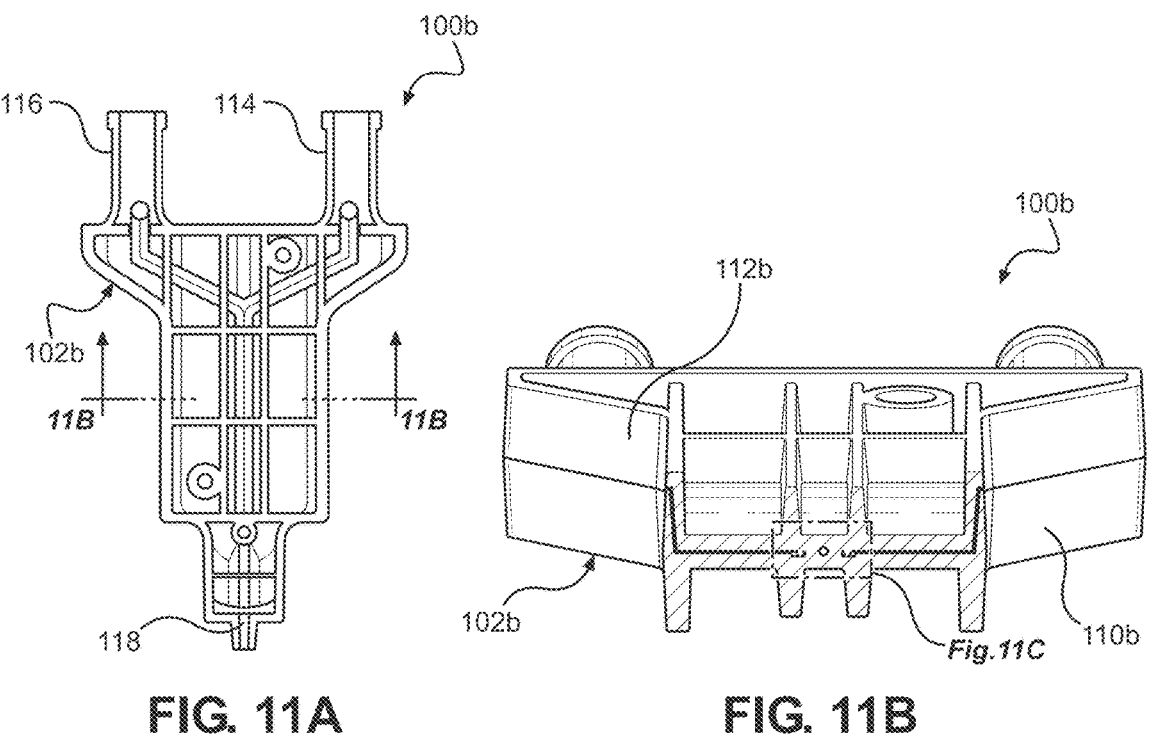
FIG. 11C illustrates an enlarged view of a region of the adapter of FIG. 11B.
Figure 11C:
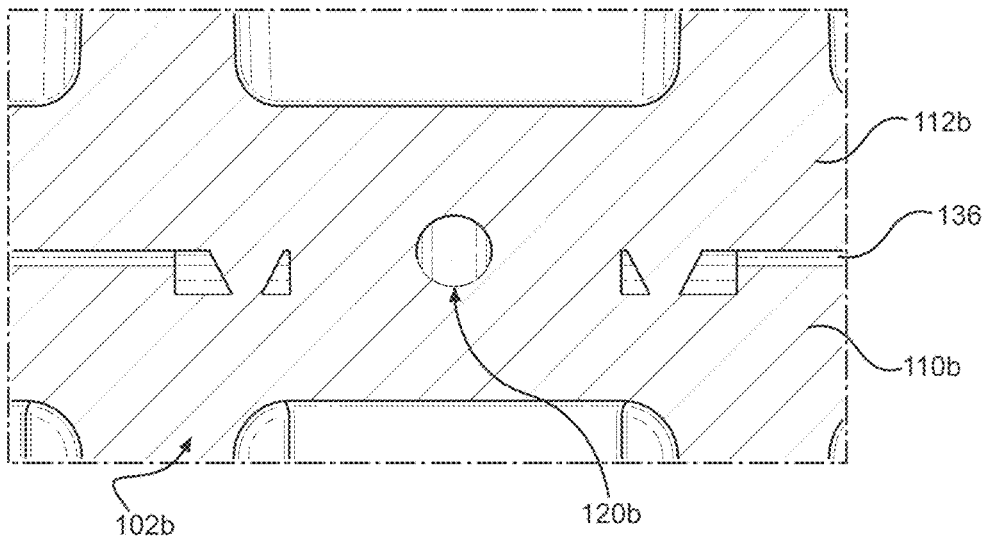

FIGS. 10-11C show other views of the system 100b, described above. The system 100b shown in FIGS. 10-11C and discussed as follows can include any of the features describe previously with respect to any of system 100a and system 100b, and vice versa. For example, the system 100b can include the adapter 102b, the first port 114, the second port 116, and the third port 118. The adapter 102b can be formed of the first piece 110b and the second piece 112b, which can be fixed together with fasteners. The first piece 110b and the second piece 112b can be injection molded and can include a two-shot sealing feature, such as a gasket 136. The first piece 110b and the second piece 112b can be formed of metal (e.g., Aluminum) or plastic (e.g., polyethylene terephthalate), among other potential material possibilities. The mixing channel 120b can be formed between the first piece 110b and the second piece 112b. That is, geometries formed into each of the first piece 110b and the second piece 112b can define the mixing channel 120b. The system 100b can be reusable.

According to a first aspect of the present disclosure, there is provided an adapter for connecting one or more storage containers with a syringe. The adapter comprises a first port configured to provide a connection with a first container volume, a second port configured to provide a connection with a second container volume, and a third port configured to provide a connection to a syringe. The adapter further comprises a mixing channel extending from a first end in fluid communication with the third port to a second end. The mixing channel comprises a tortuous path along at least a portion of its length. By providing a tortuous path in an adapter, it can be possible to use turbulence induced in the flow of fluid through the mixing channel to mix components from separate volumes as they are drawn through the adapter into a syringe. This can provide a consistent, safe, and convenient method of mixing components for injection.

Optionally, the mixing channel is a microfluidic mixing channel and may have an inner dimension (e.g., a first inner dimension) of between 20-200 μm, preferably between 20-100 μm, more preferably 20-50 μm and more preferably approximately 50 μm. Additionally, the mixing channel may have a second inner dimension (e.g., within a portion of the mixing channel) which is larger than the first inner dimension. For instance, the second inner dimensions can be between 20-500 μm, preferably between 50-200 μm, more preferably greater than or equal to 50 μm, more preferably greater than or equal to 100 μm, more preferably greater than or equal to the first inner dimension. In other words, the cross-sectional area of the channel may vary along its length.

In some embodiments, the mixing channel comprises a constriction, wherein the constriction is a portion of the mixing channel which has a smaller inner dimension than the preceding and succeeding portions of the mixing channel. In other words, the constriction is a portion of the mixing channel which is thinner than the portions of the mixing channel either side of it. The constriction can be formed as a pinch point in a length of channel, or it can be formed by alternating the cross-sectional area between a larger cross-sectional area (e.g., for channel segments extending in a first direction) and a smaller cross-sectional area (e.g., for channel segments extending in a second direction). Introducing one or more constrictions along the length of the path along which the fluid travels may further improve mixing.

Further, in some embodiments, the tortuous path is configured to induce localized changes in the flow direction of liquid moving through the mixing channel.

In some embodiments, the adapter further comprises a first transit channel extending from a first end in fluid communication with the first port to a second end in fluid communication with the mixing channel and a second transit channel extending from a first end in fluid communication with the second port to a second end in fluid communication with the mixing channel. The transit paths can be configured to deliver fluid from the container volumes to the mixing channel.

In some embodiments, the first and second transit channels have substantially the same volume. In other embodiments, the first and second transit channels have substantially different volumes. The first and second transit channels may join the mixing channel at the same point. Alternatively, the junction between the first transit channel and mixing channel and the junction between the second transit channel and the mixing channel can be offset from each other. A one-way valve can be provided between the two junctions to prevent the flow of fluid (in at least one direction) between the first and second transit channels.

The adapter may comprise a one-way valve at the second port, or between the second port and the mixing channel. Alternatively, a one-way valve need not be provided at the second port or between the second port and the mixing channel. Additionally or alternatively, the adapter may further comprise a one-way valve at the first port, or between the first port and the mixing channel.

The third port can be configured to be in bidirectional fluid communication with the syringe. For instance, the third port may comprise a rubber diaphragm configured to be pierced by a needle. Alternatively, the third port may comprise a fitting, such as a Luer taper fitting, configured to affix the syringe to the third port.

In some embodiments, the mixing channel may comprise at least one turn between sequentially connected channel portions (e.g., sequentially connected substantially straight channel portions). An angle between sequentially connected substantially straight channel portions can be less than 120 degrees, more preferably less than 100 degrees and most preferably 95 degrees or less. In one example, the angle between sequentially connected channel portions is 90 degrees so that the at least one turn forms a square junction between sequentially connected channel portions. In other embodiments, a triangular junction can be formed between sequentially connected channel portions or a sawtooth junction can be formed between sequentially connected channel portions. In other words, the at least one turn may comprise a sharp junction with bends including a discontinuity in their gradient to induce a change in the direction of fluid flow through the mixing channel. A 'sharp' bend refers to an angle between two sequentially connected (and substantially straight) sections of the mixing channel, wherein the angle is less than 120 degrees. Note that a 'sharp' bend need not comprise a vertex between two adjacent straight segments (although this is the configuration of some embodiments). Rather, a curved bend or smooth junction having a small radius of curvature can be used to connect adjacent segments. In some examples, a bend having a radius of curvature approximately equal to a width of the mixing channel can be appropriate.

In some embodiments, substantially half of the sequentially connected channel portions can be oriented in a first direction. Each of the sequentially connected channel portions may extend 1 millimeter or less, 500 μm or less, 200 μm or less, 100 μm or less, 75 μm or less, or 50 μm or less. Similarly, in some embodiments, substantially half of the sequentially connected channel portions can be oriented in a second direction, perpendicular to the first direction and/or may extend 1 millimeter or less, 500 μm or less, 200 μm or less, 100 μm or less, 75 μm or less, or 50 μm or less. Any of the sequentially connected channel portions may extend 50 μm or more, 75 μm or more, or 100 μm or more. In some embodiments, the substantially half of the sequentially connected channel portions which are oriented in the first direction extend for a smaller distance than the substantially half of the sequentially connected channel portions which are oriented in the second direction. The shorter channel portions may also have a reduced cross-sectional area than the longer channel portions to introduce a plurality of constrictions in the flow path for the fluid to further improve mixing.

The mixing channel may comprise at least 2 turns, more preferably 4 or more turns, or most preferably 10 or more turns. The mixing channel may comprise 100 turns or less, preferably 70 turns or less, or most preferably 40 turns or less. The exact number of turns of the mixing channel can be selected to achieve desired mixing, which is dependent on the geometry of the turns and the mixing channel as a whole. Therefore, in some embodiments described herein, more than 2 turns, more than 4 turns or preferably more than 10 turns and/or less than 120 turns, less than 80 turns or preferably less than 40 turns provides desired mixing and thus the mixing channel can be configured as such.

In some embodiments the adapter comprises a plurality of mixing channels. Each mixing channel in this plurality of mixing channels is configured to provide fluid communication between the first and second transit channels and the third port. In other words, the mixing channel can comprise multiple branches, each configured to provide a tortuous path for mixing fluid from the first and second container volumes. Alternatively, the adapter may only comprise one mixing channel.

In some embodiments, a further first transit channel and a further second transit channel can be provided. The further first and second transit channels can be in fluid communication with the third port via one or more mixing channels, thus providing additional fluid pathways in which fluid from the first and second container volumes can mix as they move through the adapter.

In some embodiments, the second end of the first transit channel, the second end of the second transit channel and the second end of the mixing channel meet at a meeting point. Alternatively, in some embodiments, the second end of the first transit channel meets the second end of the mixing channel, and the second end of the second transit channel meets the mixing channel offset from the second end of the mixing channel. By providing such an offset, a resistance can be enabled which reduces the entry of a fluid into the first container, or a one-way valve can be provided within the offset. The offset may additionally have the benefit of enabling the adapter to be manufactured less intricately and therefore more efficiently and cost effectively.

According to a second aspect of the present disclosure, there is provided a system. The system comprises an adapter as described in accordance with the first aspect, a first container connected to the first port; and a second container connected to the second port. The first container and the second container are fixed-volume containers.

Optionally, the first container may hold an organic compound in at least 25% alcohol, preferably at least 25% ethanol. The organic compound is optionally a lipid. Optionally still, the second container may hold a dehydrated pharmaceutical composition, preferably a lyophilized pharmaceutical composition, more preferably lyophilized RNA. Alternatively, the second container may comprise RNA in a solution, such as an aqueous solution.

The lipid in at least 25% alcohol and the RNA in a lyophilized state or as a solution can be stored and transported at conventional, e.g., room, temperatures. As such, the adapters and systems disclosed herein may enable the obstacles associated with storing and transporting RNA-LNP complexes at prohibitively low temperatures to be mitigated. Rather, each component part of the RNA-LNP complex can be stored and transported at room temperatures and subsequently the RNA-LNP can be formed via any of the adapters disclosed herein adapters at the point-of-use.

In some embodiments, the first container and the second container are removably connected to the first port and the second port respectively. Alternatively, the first container and the second container can be permanently connected to the first port and the second port respectively. The adapter can be configured to enter a locked connection with one or more containers to prevent reuse of the adapter.

Optionally, a syringe can be connected to the third port. The syringe may hold a buffer, preferably an aqueous buffer. In these embodiments a one-way valve can be provided at the second port of the adapter. Alternatively, if no one-way valve is provided the lipid can be provided in greater than 25% alcoholic solution, preferably greater than 40% alcoholic solution, and preferably greater than 60% alcoholic solution. Optionally the alcoholic solution can be ethanolic solution. Providing the lipid in such an increased concentration of alcohol can allow the lipid in alcoholic solution to withstand dilution by the reconstituting agent without affecting the quality of the resulting mRNA-LNP complex.

The adapter can be provided as part of a kit with at least one of the syringe and the containers.

According to a third aspect of the present disclosure, there is provided a method of mixing two constituents of a pharmaceutical complex via an adapter. The adapter comprises a first port connected to a first container holding a first constituent, a second port connected to a second container holding the second constituent, a third port configured to provide a connection to a syringe, a mixing channel extending from a first end in fluid communication with the third port to a second end, a first transit channel extending from a first end in fluid communication with the first port to a second end in fluid communication with the mixing channel, a second transit channel extending from a first end in fluid communication with the second port to a second end in fluid communication with the mixing channel. The mixing channel comprises a tortuous path along at least a portion of its length. The method comprises connecting a syringe comprising a plunger to the third port and withdrawing the plunger. Withdrawing the plunger draws the first constituent from the first container into the first transit channel and the second constituent from the second container into the second transit channel. Withdrawing the plunger further draws the first and second constituent into the syringe via the mixing channel.

Once the first and second constituents are drawn into the syringe via the mixing channel the pharmaceutical complex can be stored within the syringe.

Optionally, the first constituent is an organic compound in at least 25% alcohol solution and the second constituent is a dehydrated pharmaceutical composition. The organic compound is optionally a lipid. The adapter may further comprise a one-way valve at the second port, or between the second port and the mixing channel. Alternatively, if no one-way valve is provided, the lipid can be provided in greater than 25% alcoholic solution, preferably greater than 40% alcoholic solution, and preferably greater than 60% alcoholic solution. Optionally the alcoholic solution can be ethanolic solution.

Optionally, the syringe may initially hold an aqueous buffer. Here, the method may further comprise, prior to withdrawing the plunger, depressing the plunger. Here, depressing the plunger may transfer at least a portion of the aqueous buffer into the second container. In some embodiments, the method of mixing two constituents may further comprise, prior to connecting the syringe to a third port of an adapter, connecting the first container to the first port, and connecting the second container to a second port of an adapter.

In some embodiments, the method of mixing further comprises disconnecting the syringe from the third port and transferring the pharmaceutical complex from the syringe for analysis or dilution. Alternatively, the method may further comprises disconnecting the syringe from the third port and using the pharmaceutical complex directly.

According to a fourth aspect of the present disclosure, there is provided a method of manufacturing an adapter for connecting two or more containers with a syringe. The method comprises fashioning a first depression in a first polymer piece and fusing the first polymer piece to a second polymer piece such that the first depression provides at least a portion of a mixing channel extending from a first end to a second end. The mixing channel comprises a tortuous path along at least a portion of its length.

In some embodiments, the first depression comprises a discontinuous depression. In other words, the first depression may comprise a series of depressions separated from each other by space, thereby forming the discontinuity. The method of manufacturing may further comprise fashioning a second discontinuous depression in the second polymer piece. Here, using the at least two polymer pieces comprises offsetting the first discontinuous depression and the second discontinuous depression such that the second depression provides at least a portion of the mixing channel, wherein optionally the at least two polymer pieces are offset by 20 to 200 μm.

Optionally, the first and second depressions can be fashioned by injection or compression molding. Alternatively, the first and second depression may comprise a laser cut polymer film adhered on injection molded pieces.

The first and/or second depressions may provide a first transit channel extending from a first end in fluid communication with the first port to a second end in fluid communication with the mixing channel, and a second transit channel extending from a first end in fluid communication with the second port to a second end in fluid communication with the mixing channel.

It will be understood that certain terminology is used in the preceding description for convenience and is not limiting. The terms "a", "an" and "the" should be read as meaning "at least one" unless otherwise specified. The term "comprising" will be understood to mean "including but not limited to" such that systems or method comprising a particular feature or step are not limited to only those features or steps listed but may also comprise features or steps not listed. Equally, terms such as "over", "under", "front", "back", "right", "left", "top", "bottom", "side" and so on are used for convenience in interpreting the drawings and are not to be construed as limiting.

It will also be appreciated by those skilled in the art that modifications can be made to the example embodiments described herein without departing from the invention. Structural features of systems and apparatuses described herein can be replaced with functionally equivalent parts or omitted entirely. Moreover, it will be appreciated that features from the embodiments can be combined with each other without departing from the disclosure.

What is claimed is:

1. An adapter comprising:
a body;
a first port configured to connect with a first container;
a second port configured to connect with a second container; and
a third port configured to connect with a third container, wherein:
the body defines a mixing channel extending from a first end, in fluid communication with the third port, to a second end,
the mixing channel comprises a pathway that is cylindrically shaped,
the mixing channel comprises dimples that extend radially outwardly beyond the pathway and into the body, and
fluid follows a tortuous path along a longitudinal axis of the adapter into and out of the dimples and the pathway when the fluid flows through the mixing channel.

2. The adapter of claim 1, wherein the mixing channel is a microfluidic channel.

3. The adapter of claim 1, wherein the dimples surround the pathway.

4. The adapter of claim 1, wherein the dimples are arranged in sets that extend along the longitudinal axis.

5. The adapter of claim 4, wherein each set of the sets comprises two circumferential rows of the dimples that are angularly offset relative to each other about the longitudinal axis of the adapter.

6. The adapter of claim 1, wherein the mixing channel has an inner dimension of between 200 μm and 800 μm.

7. The adapter of claim 1, further defining:
a first transit channel that connects the first port with the mixing channel; and
a second transit channel that connects the second port with the mixing channel.

8. The adapter of claim 7, wherein:
the mixing channel is one of a plurality of mixing channels, and each of the plurality of mixing channels connects the first transit channel and the second transit channel to the third port.

9. The adapter of claim 1, further comprising a one-way valve connected to the second port.

10. The adapter of claim 1, wherein the third port is configured to be in bidirectional fluid communication with the third container.

11. A system comprising:
the adapter of claim 8;
the first container containing lyophilized RNA;
the second container; and
a syringe.

12. The system of claim 11, wherein the second container contains an alcohol-dissolved lipid component.

13. The system of claim 11, wherein the syringe contains a buffer.

14. A method of mixing two constituents of a pharmaceutical complex via an adapter, the adapter comprising:
a first port connected to a first container holding a first constituent of the two constituents;
a second port connected to a second container holding a second constituent of the two constituents;
a third port configured to connect to a syringe;
wherein the adapter defines a mixing channel extending from a first end in fluid communication with the third port to a second end;
a first transit channel that connects the first port with the mixing channel;
a second transit channel that connects the second port with the mixing channel,
wherein the mixing channel comprises a tortuous path along a longitudinal axis of the adapter,
the method comprising:
connecting the syringe comprising a plunger to the third port; and
withdrawing the plunger, wherein withdrawing the plunger draws the first constituent from the first container into the first transit channel and the second constituent from the second container into the second transit channel, wherein withdrawing the plunger further draws the first and second constituent into the syringe via the mixing channel.

15. The method of claim 14, wherein the first constituent is an organic compound in at least 25% alcohol solution and the second constituent is a dehydrated pharmaceutical composition.

16. The method of claim 14, the syringe initially holding an aqueous buffer, the method further comprising, prior to withdrawing the plunger, depressing the plunger, wherein depressing the plunger transfers at least a portion of the aqueous buffer into the second container.

17. The method of claim 14, the method further comprising, prior to connecting the syringe to the third port, connecting the first container to the first port, and connecting the second container to the second port.

18. A method of manufacturing an adapter, the method comprising:
forming a first depression in a first polymer piece, the first depression comprising a first discontinuous depression;
forming a second depression in a second polymer piece, the second depression comprising a second discontinuous depression; and
fusing the first polymer piece to the second polymer piece, wherein fusing the first polymer piece to the second polymer piece comprises offsetting the first discontinuous depression and the second discontinuous depression to define a mixing channel from a first end to a second end, the mixing channel comprises a tortuous path along a longitudinal axis of the adapter.

19. The method of manufacturing of claim 18, wherein the offsetting comprises offsetting the first polymer piece and the second polymer piece by an amount between about 100 μm and about 200 μm.

20. The method of manufacturing of claim 18, wherein:

forming the first discontinuous depression comprises injection molding or compression molding the first discontinuous depression, and forming the second discontinuous depression comprises injection molding or compression molding the second discontinuous depression.

* * * * *